(12) United States Patent
Peng et al.

(10) Patent No.: US 10,429,467 B2
(45) Date of Patent: Oct. 1, 2019

(54) BIOSENSOR, PALM-SIZED DEVICE AND METHOD BASED ON MAGNETIC RESONANCE RELAXOMETRY

(71) Applicants: MASSACHUSETTS INSTITUTE OF TECHNOLOGY, Cambridge, MA (US); Lan Chen, Singapore (SG)

(72) Inventors: Weng Kung Peng, Singapore (SG); Jongyoon Han, Cambridge, MA (US); Lan Chen, Singapore (SG)

(73) Assignees: MASSACHUSETTS INSTITUTE OF TECHNOLOGY, Cambridge, MA (US); NANYANG TECHNOLOGICAL UNIVERSITY, Singapore (SG)

( * ) Notice: Subject to any disclaimer, the term of this patent is extended or adjusted under 35 U.S.C. 154(b) by 1347 days.

(21) Appl. No.: 14/497,233

(22) Filed: Sep. 25, 2014

(65) Prior Publication Data
US 2015/0177348 A1   Jun. 25, 2015

Related U.S. Application Data

(63) Continuation of application No. PCT/SG2012/000056, filed on Feb. 27, 2012.
(Continued)

(51) Int. Cl.
*G01V 3/00*   (2006.01)
*G01R 33/44*   (2006.01)
(Continued)

(52) U.S. Cl.
CPC .......... *G01R 33/448* (2013.01); *G01N 24/08* (2013.01); *G01R 33/302* (2013.01);
(Continued)

(58) Field of Classification Search
CPC .................................................... G01R 33/448
(Continued)

(56) References Cited

U.S. PATENT DOCUMENTS

| | | | | |
|---|---|---|---|---|
| 4,694,254 A | * | 9/1987 | Vatis | G01R 33/3607 324/309 |
| 5,099,206 A | * | 3/1992 | Imaizumi | G01R 33/4641 324/300 |

(Continued)

*Primary Examiner* — Louis M Arana
(74) *Attorney, Agent, or Firm* — Steptoe & Johnson LLP

(57) ABSTRACT

In accordance with one aspect of this disclosure, there is provided a device for performing magnetic resonance relaxometry. The device comprises a radio-frequency spectrometer comprising at least one field-programmable gate array chip; a power amplifier electrically connected with the radio-frequency spectrometer and amplifying an electrical output of the radio-frequency spectrometer, thereby producing an amplified electrical signal comprising between about 0.1 Watts and about 10 Watts power; a duplexer configured to isolate the radio-frequency spectrometer from the amplified electrical signal during a receiving mode of the device; a radio-frequency detection probe configured to transmit radio-frequency electromagnetic radiation to excite nuclei under resonance during a transmission mode of the device, the radio-frequency detection probe comprising a detection coil comprising an inner diameter of less than about 1 millimeter; and at least one magnet supplying an external magnetic field to a detection region of the radio-frequency detection probe, the external magnetic field being less than about 3 Tesla.

17 Claims, 23 Drawing Sheets

Related U.S. Application Data

(60) Provisional application No. 61/447,339, filed on Feb. 28, 2011.

(51) Int. Cl.
| | | |
|---|---|---|
| *G01N 24/08* | (2006.01) | |
| *G01R 33/30* | (2006.01) | |
| *G01R 33/50* | (2006.01) | |
| *G01R 33/383* | (2006.01) | |
| *G01R 33/48* | (2006.01) | |
| *G01R 33/54* | (2006.01) | |
| *G01R 33/38* | (2006.01) | |
| *G01R 33/465* | (2006.01) | |
| *A61B 5/055* | (2006.01) | |

(52) U.S. Cl.
CPC ....... *G01R 33/383* (2013.01); *G01R 33/4828* (2013.01); *G01R 33/50* (2013.01); *G01R 33/543* (2013.01); *G01R 33/546* (2013.01); *A61B 5/055* (2013.01); *G01R 33/3808* (2013.01); *G01R 33/465* (2013.01)

(58) Field of Classification Search
USPC .................................................. 324/322, 318
See application file for complete search history.

(56) References Cited

U.S. PATENT DOCUMENTS

| | | | |
|---|---|---|---|
| 6,696,838 B2 * | 2/2004 | Raftery ................. | G01R 33/307 324/310 |
| 7,180,295 B2 * | 2/2007 | Tanaka ................. | G01R 33/341 324/321 |
| 8,692,548 B2 * | 4/2014 | Hoyt .................... | G01R 33/305 324/307 |

* cited by examiner (b)

(c)

| Parameters | Microscopy | PCR | Dipstick | MRR |
|---|---|---|---|---|
| Sensitivity (parasites/uL) | 50 (thick film) | 5 | >100 | 10-50 |
|  | 200 (thin-film) |  |  |  |
| Parasitemia (Quantitative) | Yes | No | Estimation | Classification based |
| Parasite stages (Qualitative) | Yes | Yes (DNA level) | No | on severity index |
| Time (Sample detection) | 30-60 min | 24 hr | 20 min | 1-2 min |
| Sample preparation | 10-20 min (tedious) | tedious and highly skillful job | minimal | (3-5 min) minimal, parallel processing possible |
| Equipment | Microscope | PCR apparatus | Kit only | Benchtop MRR |
| Cost per test | Low | High | Moderate | Low |

Fig. 22

BIOSENSOR, PALM-SIZED DEVICE AND METHOD BASED ON MAGNETIC RESONANCE RELAXOMETRY

CLAIM OF PRIORITY

This continuation application claims priority to International Application No. PCT/SG2012/000056, filed on Feb. 27, 2012, which claims priority to U.S. Provisional Application Ser. No. 61/447,339, filed Feb. 28, 2011, each of which is incorporated by reference in its entirety.

BACKGROUND OF THE INVENTION

Malaria is one of the most lethal infectious diseases in tropical countries, with 300 to 500 million new cases and about 2 million deaths every year (16). Four protozoan species of *Plasmodium* infect human beings: *Plasmodium falciparum, Plasmodium vivax, Plasmodium malariae*, and *Plasmodium ovale*. Among these, *P. falciparum* parasites are the most common and infectious, causing 90% of the total deaths.

The current "gold standard" for malaria diagnosis is the microscopic examination of Giemsa stained blood smears (17) either in the form of thick films or thin films. Such microscopic techniques allow the identification of the different stages of infection and quantification of parasitemia level (ratio of infected red blood cells (iRBCs) over total number of red blood cells (RBCs)). Using a thick blood film, a well trained microscopist may be able to identify up to 0.001% parasitemia (about 50 parasites/µL of blood). However, most routine diagnostics in traditional laboratories generally achieve a much lower sensitivity of about 0.01% of parasitemia (18). Practically, the sensitivity limit is often much lower due to the unavailability of well trained technicians (or equipment), particularly in non-endemic areas (or isolated places), and the unavailability of fresh reagents in resource poor settings (19, 20). Besides, slide preparation is time consuming and labor intensive (about 30 minutes), followed by another 20 to 30 minutes of manual cell counting which is prone to human error (e.g., misinterpretation) or artifacts from the stain (18, 20).

Other non-microscopy-based malaria diagnostic techniques, such as polymerase chain reaction (PCR), have much higher sensitivity and specificity, but require extensive procedures, high levels of expertise and well equipped laboratories and thus are not ideal for on field settings (21). On the other hand, rapid diagnostic tests (dipsticks) based on lateral flow immunoassay, which detect parasite-specific proteins from blood, suffer from the inability to provide a quantitative parasitemia level (18, 19). Accurate determination of parasitemia is important for managing infection relapse or recrudescence, as well as for ascertaining drug and treatment efficacy. As there are no vaccines for malaria and with the fast emergence of chloroquine resistant species, there is an increasing need for a simple tool to quantify parasitemia levels reliably (22, 23).

Separately, in the field of magnetic resonance devices, bulky-sized, expensive and high-maintenance superconducting magnets, spectrometers and power amplifiers remain bottlenecks in the realization of compact and portable magnetic resonance devices, and prevent the use of magnetic resonance devices in on-site analysis. Coupled with strict requirements for high field homogeneity, which demands tedious shimming protocols and parameter settings, the practical usage of magnetic resonance has often been reduced to work in research laboratories by well-trained personnel. Even a commercial state of the art bench-top nuclear magnetic resonance (NMR) spectrometer typically weights a few kilograms. Thus, while there have been developments in making magnetic resonance systems more compact (1-12), there is an ongoing need to reduce the cost per test, affordability and portability of magnetic resonance devices.

SUMMARY OF THE INVENTION

In accordance with one aspect of this disclosure, there is provided a device for performing magnetic resonance relaxometry. The device comprises a radio-frequency spectrometer comprising at least one field-programmable gate array chip; a power amplifier electrically connected with the radio-frequency spectrometer and amplifying an electrical output of the radio-frequency spectrometer, thereby producing an amplified electrical signal comprising between about 0.1 Watts and about 10 Watts power; a duplexer configured to isolate the radio-frequency spectrometer from the amplified electrical signal during a receiving mode of the device; a radio-frequency detection probe configured to transmit radio-frequency electromagnetic radiation to excite nuclei under resonance during a transmission mode of the device, the radio-frequency detection probe comprising a detection coil comprising an inner diameter of less than about 1 millimeter; and at least one magnet supplying an external magnetic field to a detection region of the radio-frequency detection probe, the external magnetic field being less than about 3 Tesla.

In further, related embodiments, the at least one magnet may comprise at least two permanent magnets separated by a gap of less than about 5 millimeters. The device may weigh less than about 0.5 kilograms. The radio-frequency spectrometer, power amplifier and the at least one magnet may be mounted on a single circuit board of less than about 500 square centimeters size. The device may be capable of detecting a nuclear magnetic resonance electromagnetic signal for at least a substantial portion of a blood sample of volume less than about 100 nanoliters in less than about 1 minute. The radio-frequency spectrometer may comprise a pulse programmer, a direct digital synthesis module, the transmitter and a receiver. The power amplifier may be mounted on a single circuit board of less than about 20 square centimeter area. The at least one magnet may fit within a volume of less than about 30 cubic centimeters. The duplexer may comprise a passive duplexer without a quarter wavelength transmission cable, the passive duplexer comprising: a chip inductor in parallel with a fixed capacitor that is in series with a pair of crossed diodes; a trimmer capacitor in series with the parallel combination of the chip inductor, fixed capacitor and pair of crossed diodes; and at least one surface mount radio frequency switch diode. The device may be configured to receive a centrifuge tube, which same centrifuge tube is configured to be received in a centrifuge. The device may further comprise a centrifuge tube, at least a portion of the centrifuge tube being inserted into the detection region of the radio-frequency detection probe. The centrifuge tube may comprise an outside diameter of less than about 1 millimeter, and may comprise a blood sample including blood from an animal body. The blood sample may comprise a volume of less than about 100 nanoliters. The power amplifier may comprise at least one surface mount power amplifier module. The device may be configured to perform at least one of Nuclear Magnetic Resonance (NMR) and Magnetic Resonance Imaging (MRI).

In further related embodiments, the device may comprise a sample comprising a micro-organism. At least a portion of the sample may be inserted into the detection region of the radio-frequency detection probe. The device may comprise an item to be imaged, at least a portion of the item to be imaged being inserted into the detection region of the radio-frequency detection probe. The device may further comprise a biological sample, at least a portion of the biological sample being inserted into the detection region of the radio-frequency detection probe. The biological sample may be capable of producing an indication of a stress level on a biological organism through magnetic resonance. The biological sample may comprise a biomarker of a disease, the biomarker being detectable by magnetic resonance.

In accordance with another aspect of this disclosure, there is provided a method of determining an infection level of cells in blood from an animal body using magnetic resonance relaxometry. The method comprises concentrating at least a portion of a blood sample comprising the blood from the animal body thereby producing concentrated red blood cells; inserting the concentrated red blood cells within a detection coil of a magnetic resonance relaxometry device; and determining an infection level of the cells in the blood based at least in part on a transverse relaxation rate of the concentrated red blood cells in the magnetic resonance relaxometry device.

In further, related embodiments, the determining of the infection level of the cells may be based at least in part on a change in a transverse relaxation rate of the concentrated red blood cells relative to a predetermined standard for transverse relaxation rate for blood that is not infected with a disease. The concentrating of the blood sample may comprise centrifuging the blood sample in a centrifuge tube, and the same centrifuge tube used in the centrifuging of the blood sample may be used in the inserting of the concentrated red blood cells within the detection coil of the magnetic resonance relaxometry device. The method may comprise determining infection level of red blood cells infected with hemoglobin-feeding parasites in blood from a human body; such as determining infection level for at least one of red blood cells infected with *plasmodium falciparum, plasmodium malariae, plasmodium vivax* and *plasmodium ovale* in the blood from the human body. An external magnetic field applied to the concentrated red blood cells by the magnetic resonance relaxometry device may be less than about 3 Tesla. The determining of the infection level may be performed without chemical labeling of the cells and without immuno-magnetic labeling of the cells. A detection region of the magnetic resonance relaxometry device may comprise a volume covering less than about 1 μl of the concentrated red blood cells. Determining the infection level may comprise detecting a less than 0.01% concentration of parasites in the blood. The detection coil may comprise an inner diameter of less than about 1 millimeter. The determining of the infection level of the cells may be performed within about one minute from the inserting the concentrated red blood cells within the detection coil. Determining the infection level may comprise determining a magnetic susceptibility index of the cells. The magnetic susceptibility index may be based at least in part on the transverse relaxation rate and may be related to parasitemia level and stage of infection for the cells in the blood from the animal body. The method may comprise performing at least one of Nuclear Magnetic Resonance (NMR) and Magnetic Resonance Imaging (MRI).

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments according to aspects of the present disclosure.

FIG. 22 is a table showing competitive advantageous of magnetic resonance relaxometry in accordance with one aspect of this disclosure as compared to existing technologies such as microscopy, PCR, and dipstick.

DETAILED DESCRIPTION OF THE INVENTION

A description of example embodiments follows.

In accordance with one aspect of this disclosure, there is provided a compact, lightweight, stand-alone magnetic resonance relaxometry (MRR) system that weighs less than 0.5 kg and comprises a miniaturized radio-frequency spectrometer, power amplifier and permanent magnet mounted on a single acrylic board of size 20 cm by 20 cm, at a cost less than $2500. In accordance with one aspect of this disclosure, the necessary parts are miniaturized by constructing a tablet-sized 0.76 Tesla permanent magnet, single board 1-Watt power amplifier, compact passive duplexer, and radio-frequency detection probe, in which the whole system is controlled by a single chip Field Programmable Gate Array (FPGA) based rf-spectrometer. With lower cost and increased portability, it is a goal of one aspect of this disclosure to bring magnetic resonance (MR) technology to the point-of-care level; whereby medical doctors can access the patient's condition by the bedside and can bring the system out to the field for diagnosis, especially in resource-limited settings. One aspect of this disclosure provides an MRR system that is highly sensitive, with the capability of detecting tens of nanoliters of unprocessed blood sample in less than a minute.

Overall Architecture

Figure 1:
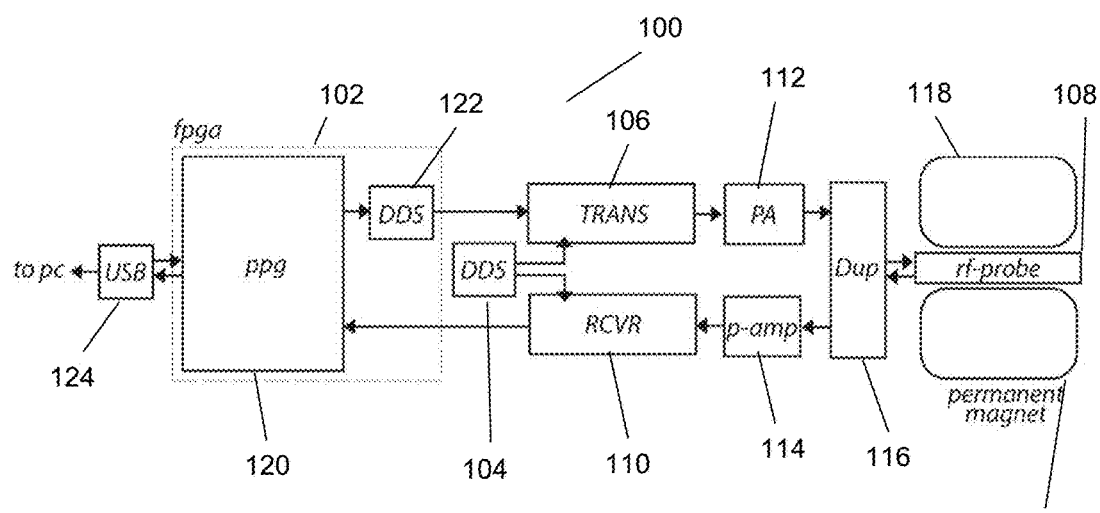
FIG. 1 is a schematic of a Magnetic Resonance Relaxometry (MRR) system in accordance with one aspect of this disclosure.

FIG. 1 is a schematic of a Magnetic Resonance Relaxometry (MRR) system 100 in accordance with one aspect of this disclosure. The system 100 comprises a Field-Programmable Gate Array-based (FPGA-based) radio frequency (rf) spectrometer 102 to control the MRR system 100, a first direct digital synthesis 104 module for generation of radio frequency pulses, a transmitter (TRANS) 106 for transmission of the generated radio frequency pulses to a radio frequency (rf) probe 108, a receiver (RCVR) 110 for receiving resonance information from the radio frequency probe 108, a first power amplifier (PA) 112, a pre-amplifier (p-amp) 114, a duplexer (Dup) 116 for transmitting a high power excitation pulse to the rf probe 108 in the transmission mode and for isolating the high power excitation pulse from the receiver 110 during receiving mode, and a magnetic system 118. In many embodiments, the FPGA-based rf spectrometer 102 comprises a pulse programmer (PPG) 120 adapted to control the FPGA-based rf spectrometer 102 and a second direct digital synthesis (DDS) 122. The second DDS 122 is to generate a fixed intermediate frequency (IF). The first DDS 104 is configured to generate a variable desired frequency. In accordance with one aspect of this disclosure, the FPGA-based spectrometer 102 may use the design set forth in Takeda K. (2007), "A highly integrated FPGA-based nuclear magnetic resonance spectrometer," *Rev Sci Instrum* 78(3):033103; and/or in Takeda K. (2008) "OPENCORE NMR: open-source core modules for implementing an integrated FPGA-based NMR spectrometer," *Journal of Magnetic Resonance* 192(2):218-229, the teachings of which two references are incorporated by reference in their entirety.

In accordance with one aspect of this disclosure, in order to facilitate processing of information to and from the MRR system 100, the FPGA-based rf spectrometer 102 is couplable to at least one external electronic device which may, for example, include a personal computer, mobile phone and/or a portable electronic tablet. Coupling between the MRR system 100 and the at least one external electronic device may be by way of at least one of USB, HDMI and/or wireless connection means 124 such as Wi-Fi and/or Bluetooth.

In conventional NMR systems, the major cost of instrumentation lies on the superconducting magnet (or permanent magnet) and rf-spectrometer. In accordance with one aspect of this disclosure, the whole system may cost less than $2500; in which the majority of the cost lies on the FPGA chip ($1000 each), external GHz-clock ($250 each), DDS (Analog-Device; AD9858, $400 each), 1-Watt power amplifier ($100), pre-amplifier ($50), RCVR (AD8343, $4 each), TRANS (AD834, $20 each, and AD8343) and USB (FT2232D, $10 each). Indicated in the parentheses is the cost of the main electronic component used. Others periphery components such as pin connectors (e.g., SMA), capacitors, rf-switches, rf-transformers and rf-filters cost less than $10 each.

In accordance with one aspect of this disclosure, the MRR system 100 may be adaptable to operate in various modes to detect NMR-active nuclei such as proton, fluorine, phosphorus and carbon. The magnetic field used in each mode in which the MRR system 100 operates depends on which nuclei are to be detected. Depending on the mode of operation, the MRR system 100 can operate at a magnetic field of between approximately 0.1 and 3 Tesla (T) which can correspond to between approximately 1 and 150 MHz. For instance, when the MRR system 100 is operating in a proton NMR mode, the magnetic field is approximately 0.76 T which corresponds to approximately 31.9 MHz for proton NMR frequency.

In accordance with one aspect of this disclosure, the MRR system 100 is controlled by the FPGA-based rf spectrometer 102 which comprises the pulse programmer 120 and the second DDS 122. As compared to CMOS technology, FPGA provides the advantages of re-programmability. As understood by a person of ordinary skill in the art, the FPGA-based rf spectrometer 102 may, for example, be programmable using tools and software provided by vendors such as Altera Corporation of San Jose, Calif., U.S.A. and Xilinx, Inc. of San Jose, Calif., U.S.A. In an exemplary embodiment, the FPGA chip 120 of this disclosure includes the EP3C80F780C8N, Cyclone III (Altera) embedded on a breadboard (ACM-202-80C8, HumanData, Japan). This chip has 81000 logic elements and is capable of producing 3 independent if-outputs, when fully utilized.

In accordance with one aspect of this disclosure, the pulse programmer 120 generates high power excitation rf pulses. The generated rf pulses then pass through the first power amplifier 112 to produce optimized rf-power for a duration of approximately between 1 and 1000 microseconds to excite all the nuclei effectively. The high power rf pulses are transmitted to the rf probe 108 and will be discussed further herein.

In an exemplary operation, power used for liquid state and solid-state NMR is approximately between 0.1 W and 10 W and approximately between 100 W and 1000 W, respectively. A "strong" power amplifier is often indispensable in MRR systems and such "strong" power amplifiers are often bulky, and require high power consumption, thereby posing serious limitation for field work. In accordance with one aspect of this disclosure, a novel and lightweight 1-Watt power amplifier is constructed on a 4 cm by 4 cm printed circuit board (see FIG. 6A). A solenoid type microcoil (inner diameter 750 μm) is further employed to generate a strong oscillating magnetic field, $B_1$, and picks up a signal from the free induction decay (FID) or spin-echo. By employing the duplexer 116, the high power excitation if pulses that are to be transmitted to the rf-probe 108 in the transmission mode can be isolated from the receiver 110 during the receiving mode. The FID/spin-echo is then amplified by a pre-amplifier 114 (AMP-75+, Mini Circuits, USA) with a gain of 20 dB and noise figure of 2.83, and finally filtered by appropriate low pass filter before going into the receiver circuit 110. FID is the observable NMR signal generated by non-equilibrium nuclear spin magnetization precessing about the static magnetic field (conventionally along z-axis). This non-equilibrium magnetisation can be induced, by applying a pulse of resonant radio-frequency close to the Larmor frequency of the nuclear spins. Spin-echo is the refocusing pulse after a single 90-degree inversion followed by inverting them by an 180-degree pulse at resonant.

Permanent Magnet

In accordance with one aspect of this disclosure, the magnet system 118 may be portable and light weight (for example, about 60 g) and adaptable to produce a high static field. The magnet system 118 may comprise at least one magnet disposed adjacent to the rf probe 108. Alternative embodiments include having at least two magnets disposed adjacent to the rf probe 108. The rf probe 108 can be disposed between the at least two magnets. The magnet system 118 can comprise a permanent magnet and/or an electromagnet. Permanent magnets used in the magnet system 118 may, for example, include Neodymium based magnets.

Figure 2:
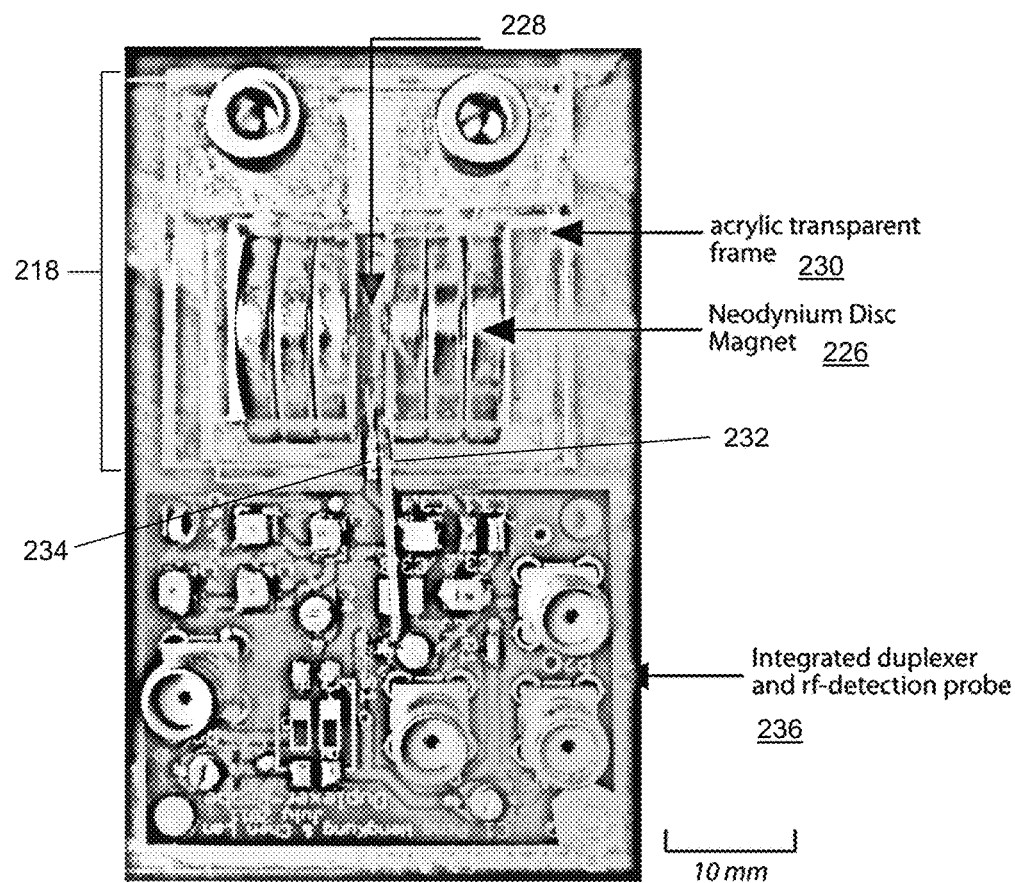
FIG. 2 is a drawing of a magnet system in accordance with one aspect of this disclosure.

FIG. 2 is a drawing of a magnet system and integrated duplexer and rf-detection probe in accordance with one aspect of this disclosure. In an exemplary embodiment, the magnet system 218 is a construction of a dipole design. In an actual device, three dipole-dipole disk-shaped Neodymium permanent magnets (Master Magnetic, Inc., USA) were arranged in stacks 226 on each side of the magnet system 218 and separated by a gap 228 of 2700 μm. More generally, one aspect of this disclosure may use at least two permanent magnets separated by a gap of less than about 5 millimeters. An acrylic transparent type of frame 230 measuring 3 cm×3 cm×2 cm was constructed to hold these magnets in place. More generally, one aspect of this disclosure may use an assembly of magnets that fits within a volume of less than about 30 cubic centimeters. Since the gap 228 is much smaller than in conventional systems, a homogenous high field concentrated in the middle of the gap 228 produced a "sweet-spot" which peaked at about 0.76 Tesla (see FIG. 3). While a smaller gap 228 is desirable in gaining a high magnetic field, it also inevitably reduces the sample volume that can be measured, thereby reducing the sensitivity. On the other hand, by restricting the same volume, homogeneity of the magnet can to a certain extent be relaxed. At least a portion of microcapillary tube 232, or other centrifuge tube, may be inserted into the gap 228. More generally, the centrifuge tube may have an outside diameter of less than about 1 millimeter. In addition, a projecting portion 234 of an integrated duplexer and rf-detection probe 236 may be slotted inside the gap 228. More generally, one aspect of this disclosure may use a radio-frequency spectrometer, power amplifier and at least one magnet mounted on a single circuit board of less than about 500 square centimeters size.

Figure 3:
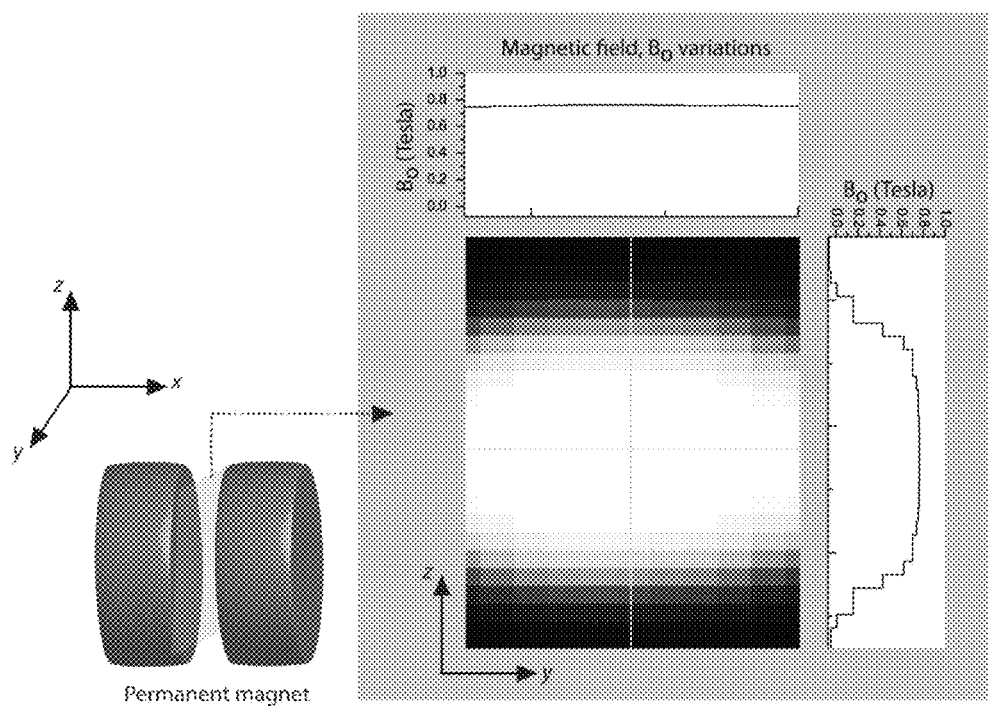
FIG. 3 is a diagram of magnetic field variations along the cross section of the magnet in accordance with one aspect of this disclosure.

FIG. 3 is a diagram of magnetic field, $B_o$, variations along the cross section of the magnet 218 as measured by gaussmeter (GM08 Hirst magnetic Instruments Ltd., UK), in accordance with one aspect of this disclosure. In this example, the "sweet spot" has a magnetic field of about 0.76 Tesla. More generally, one aspect of this disclosure may use a magnetic field of less than about 3 Tesla.

Compact and Integrated Passive Duplexer and Rf-Detection Probe

A conventional passive duplexer employs pairs of cross diodes and quarter wavelength cable in order to isolate the high rf power as it exceeds the threshold value of the cross diodes. In practice, however, especially for low frequency NMR experiment (below 35 MHz), a quarter wavelength transmission cable can be inconveniently long and not suitable for the development of a bench-top system.

Figure 4A:
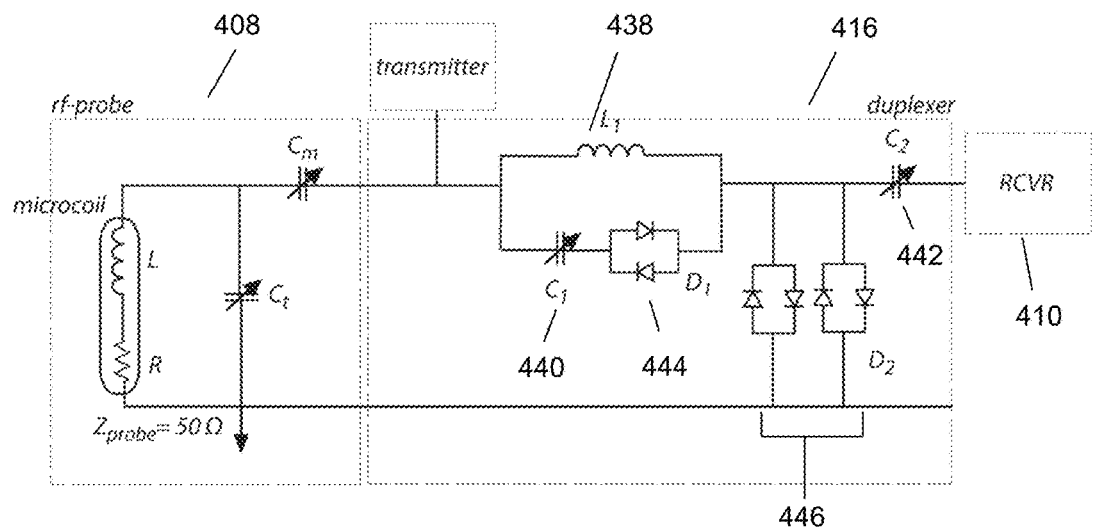
FIG. 4A is a schematic diagram of circuits for a duplexer and rf-detection probe, in accordance with one aspect of this disclosure.

FIG. 4A is a schematic diagram of circuits for a duplexer 416 and rf-detection probe 408, in accordance with one aspect of this disclosure. The conventional lengthy and bulky quarter wavelength transmission cable is replaced with a much simpler and compact resonant circuit for the duplexer 416 (13). In an actual device in accordance with one aspect of this disclosure, the resonance circuit 416 was constructed from a wire-wound chip inductor 438 (Bourns CM453232, USA) and fixed capacitor 440 (Voltronic, USA) and ceramic trimmer capacitor 442 (Murata TZ03, Japan), along with a pair of cross diodes 444. Two pairs of surface mount type RF PIN switch diodes 446 (HSMP-389c, Avago Technologies) were further employed right before the pre-amplifier of the receiver 410. The duplexer 416 and rf-probe 408 were both tuned to resonate at 31.9 MHz for proton NMR. The parameters for LC components were, $L_1$=0.47 μH, $C_1$=$C_2$=28 pF, $C_m$=870 pF, $C_1$=50 pF, and the measured Q-factor of the probe 408 is about 35.

Figure 4B:
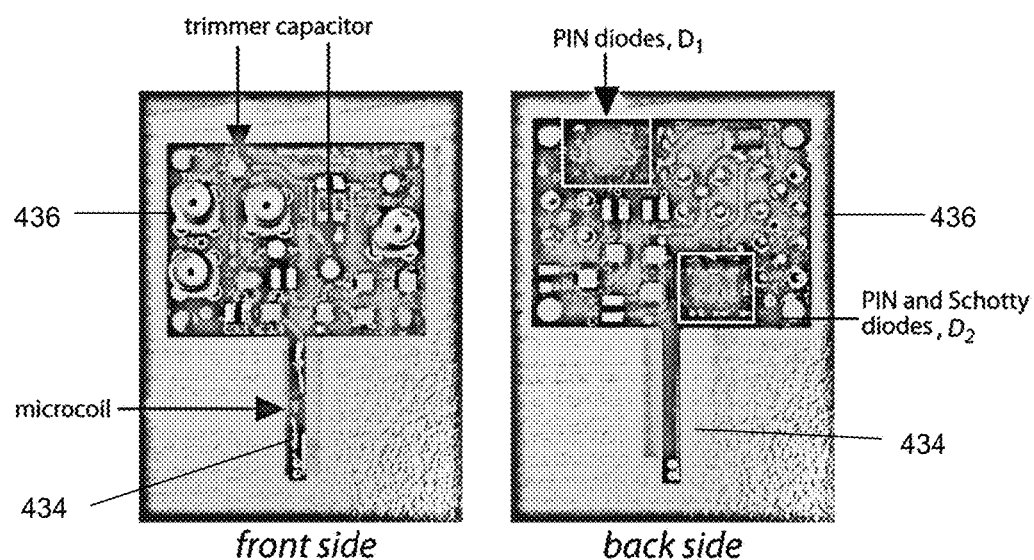
FIG. 4B is a diagram showing a front side and a back side of a duplexer and rf-probe in accordance with one aspect of this disclosure.

FIG. 4B is a diagram showing a front side and a back side of a duplexer and if-probe in accordance with one aspect of this disclosure. A projecting portion 434 of an integrated duplexer and rf-detection probe 436 may be slotted inside the gap 228 (see FIG. 2). Together with the duplexer 416, a tank circuit for the rf probe 408 may be constructed on a single printed circuit board (pcb), as shown in FIG. 4B. In an exemplary embodiment, the rf probe 408 comprises a 4-turn microcoil of inner diameter 750 μm made of single strand enameled copper wire (FA-NR 927943, Block, German) of diameter 400 μm. More generally, one aspect of this disclosure may use a detection coil comprising an inner diameter of less than about 1 millimeter. For detecting the resonance of the nuclei, the rf probe 408 was in contact with liquid samples contained in a microcapillary tube (o.d.: 730 µm) (Drummond Scientific Co., Broomall, Pa.). As little as approximately 60 nL of effective volume can be measured. Using a microcoil in the if-probe 408 increases the volume sensitivity and hence reduces the need to have high-field homogeneity. A microcoil also increases the power efficiency and hence circumvents the need to have bulky power-amplifiers. In an exemplary embodiment, with a portable 1 Watt power amplifier, a 90-degree pulse of about 50 kHz nutation field is achieved. The measured Q-factor of the probe which is about 35, is much higher than the Q-factor reported by other literatures; for example, a Q-factor of 28.5 by V. Demas et al. (8), 10 by L. Sillerud et al. (9), 24 by C. Massin et al. (14, 15), and 20.9 by N. Sun et al. (5).

Figure 5A:
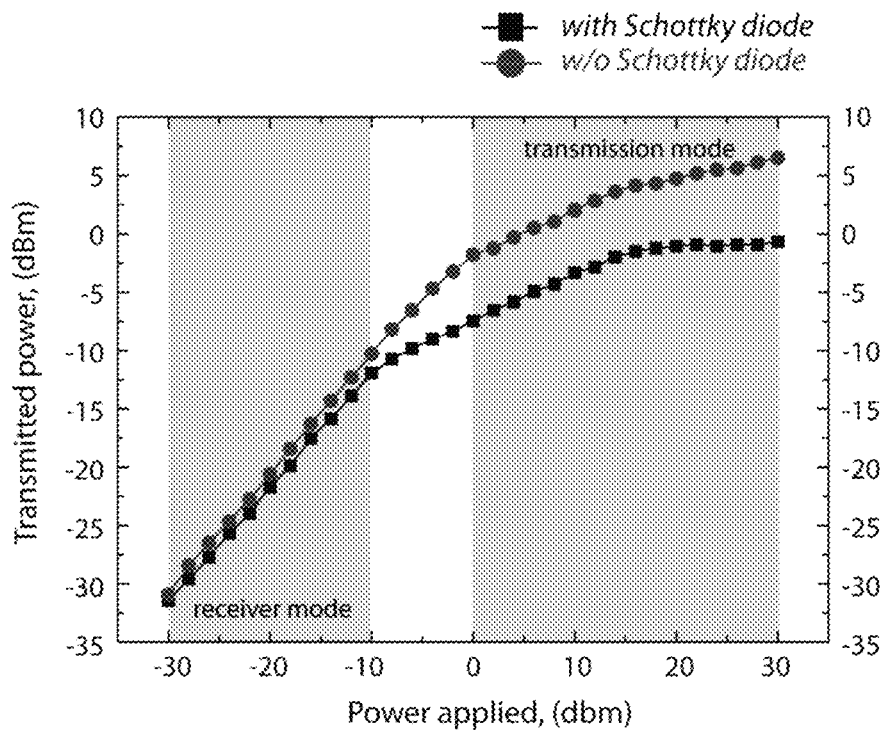
FIGS. 5A and 5B show results of an experiment in accordance with one aspect of this disclosure, in which the performance of a duplexer was evaluated by applying a range of rf-powers while measuring transmitted power at the receiver.
Figure 5B:
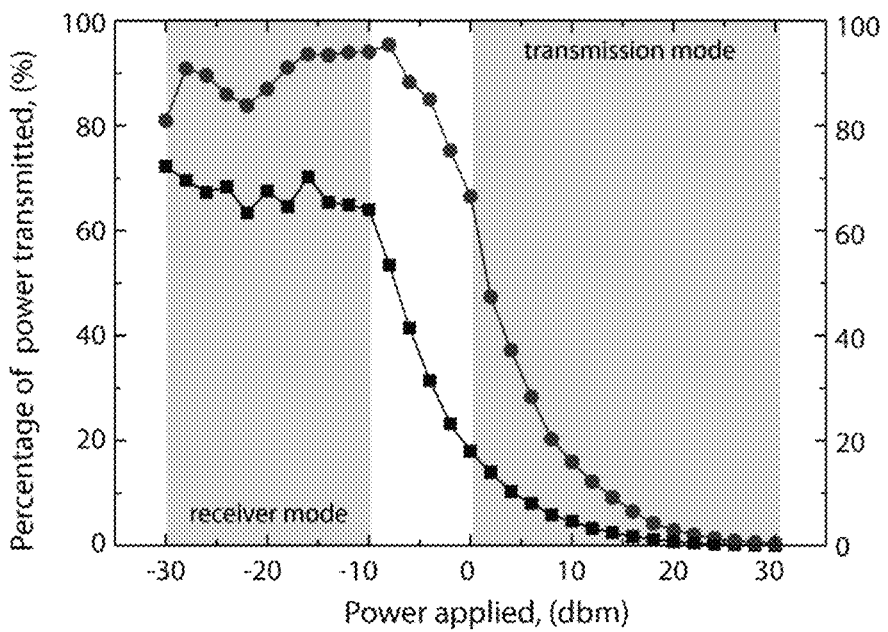

FIGS. 5A and 5B show results of an experiment in accordance with one aspect of this disclosure, in which the performance of the duplexer 416 was evaluated by applying a range of rf-powers while measuring its transmitted power at the receiver. The plots show the response rf power (−30 dbm to 30 dbm) in terms of dbm (FIG. 5A) and percentage (FIG. 5B), on the receiver as measured by oscilloscope (TDS 2012D, Tektronix, Oreg.). Rf-powers applied were supplied by spectrum analyzer (HM 1010, HAMEG, Germany). Typically, signal from free induction decay ranges from −30 dbm to −10 dbm, while high transmission rf-power ranges from 0 dbm to 30 dbm for liquid-state NMR. During the transmission mode where high rf-power is applied (e.g., 30 dbm), a power leakage to the receiver has been reduced to less than 6.5 dbm (FIG. 5A). The power leakage can be further suppressed to 0 dbm by employing an additional pair of Schottky-type diodes (HSMS-286F, Avago Technologies). This is sufficiently small as compared to the safety input level of the pre-amplifier (AMP-75+, Mini Circuits, USA), which is 13 dbm. In receiving mode, there is an insertion loss of about 10% and 30% for the case of with and without additional pair of Schottky diode, respectively (FIG. 5A). However, these losses are typically compensated by low-noise, high-gain pre-amplifier.

Single Board 1-Watt Power Amplifier

Figure 6A:
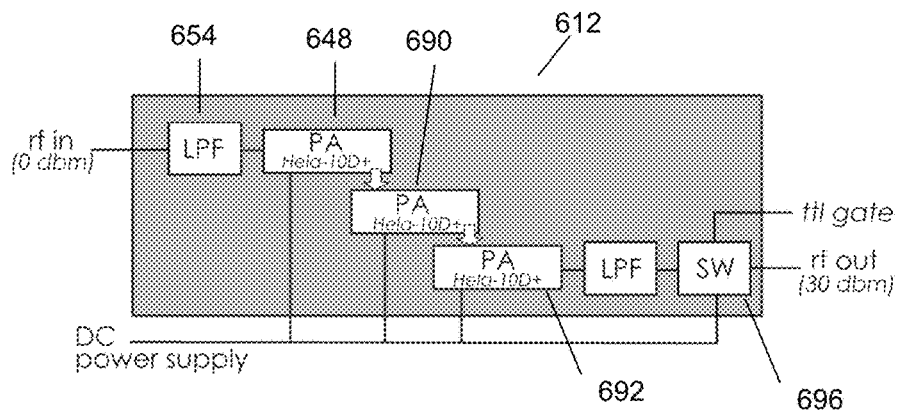
FIG. 6A is a schematic diagram of a power amplifier in accordance with one aspect of this disclosure.
Figure 6B:
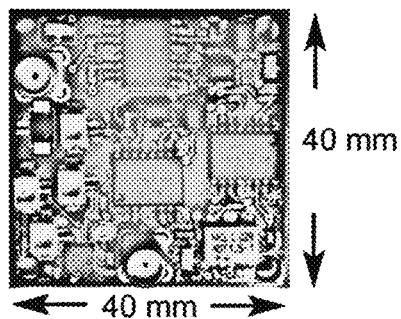
FIGS. 6B and 6C show both sides of a printed circuit board on which a power amplifier is mounted, in accordance with one aspect of this disclosure.
Figure 6C:
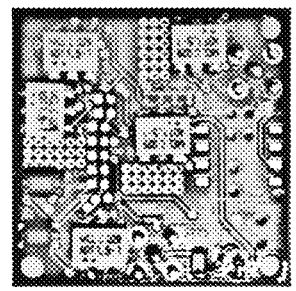

FIG. 6A is a schematic diagram of a 1-Watt power amplifier 612, in accordance with one aspect of this disclosure. In an exemplary embodiment, a cascade of three stages 648, 650, 652 of surface mount type of power amplifiers (HELA 10D+, 8-300 MHZ, 50Ω, Mini-Circuits) were packed onto a two sided 40 mm×40 mm printed circuit board, as shown in FIGS. 6B and 6C. Each core component 648-652 of the power amplifier (HELA 10D+) is capable of producing a typical gain of 11 dB and typical maximum output power of 33 dbm, which is powered by a DC power supply of +12V. Typically, a transmitter can only produce rf-power of 0 dbm. Therefore, a triple cascaded system was needed to produce a maximum amplification to 30 dbm (1 Watt) of rf-output. All of the electronic components for the power amplifier 612 were mounted on a single printed circuit board as shown in FIGS. 6B and 6C. The circuit weighed about 13 grams. More generally, one aspect of this disclosure may use a power amplifier mounted on a single circuit board of less than about 20 square centimeters area. A low pass filter 654 (LFCN-105+, Mini-Circuits) with cut-off frequency at 105 MHz was inserted before the input of each amplifier stage and the output of the PA. A surface mount type high-power switch 656 (HSWA2-30DR+, Mini-Circuits) employed before the output port was an absorptive RF switch. This switch 656 is controlled by a signal (TTL) to synchronize with the rf input pulse sequence, which can further reduce noise leakage to the receiver, especially in the receiving mode.

Figure 7:
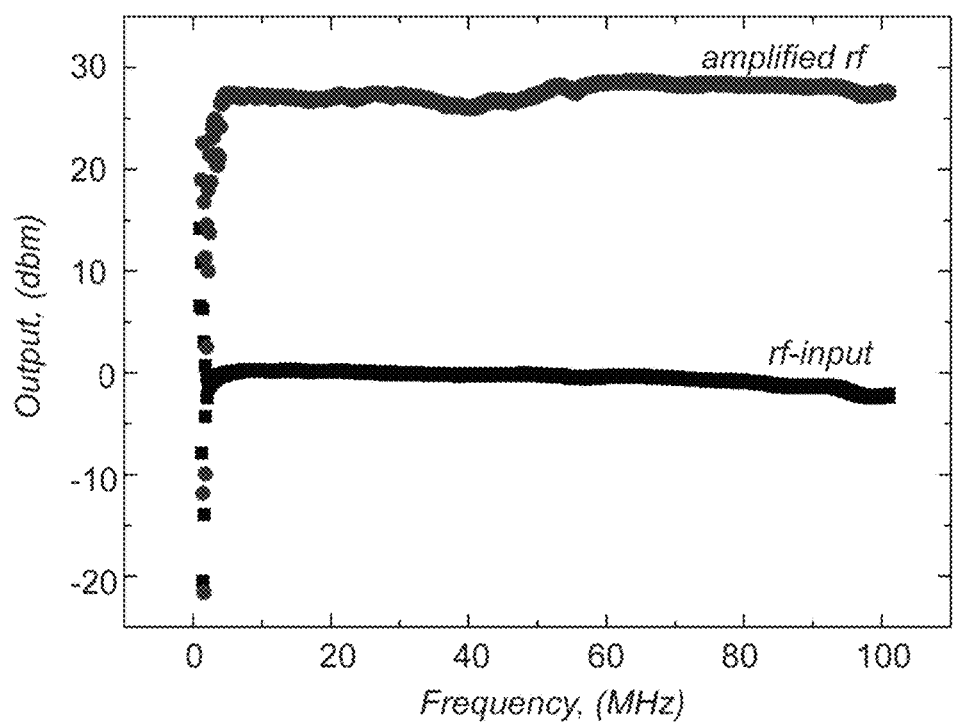
FIG. 7 is a plot showing the output of a power amplifier in accordance with one aspect of this disclosure, showing power amplified over a frequency range of 8-100 MHz.

FIG. 7 is a plot showing the output of a power amplifier in accordance with one aspect of this disclosure, showing power amplified over a frequency range of 8-100 MHz. The actual working frequency of HELA-10D+, used in an exemplary embodiment, ranges from 8 MHz to 300 MHz. In the exemplary embodiment, however, the upper frequency limit was limited by the low pass filter 654, which has cut-off at 105 MHz. The performance of the power amplifier was measured by a spectrum analyzer (HM 1010, HAMEG, Germany). An attenuator of −20 dB was used to protect the receiver of the spectrum analyzer, resulting in 1 dB of insertion loss. The y-axis shown in the graph was scaled back 20 dB due to the attenuator.

Figure 8A:
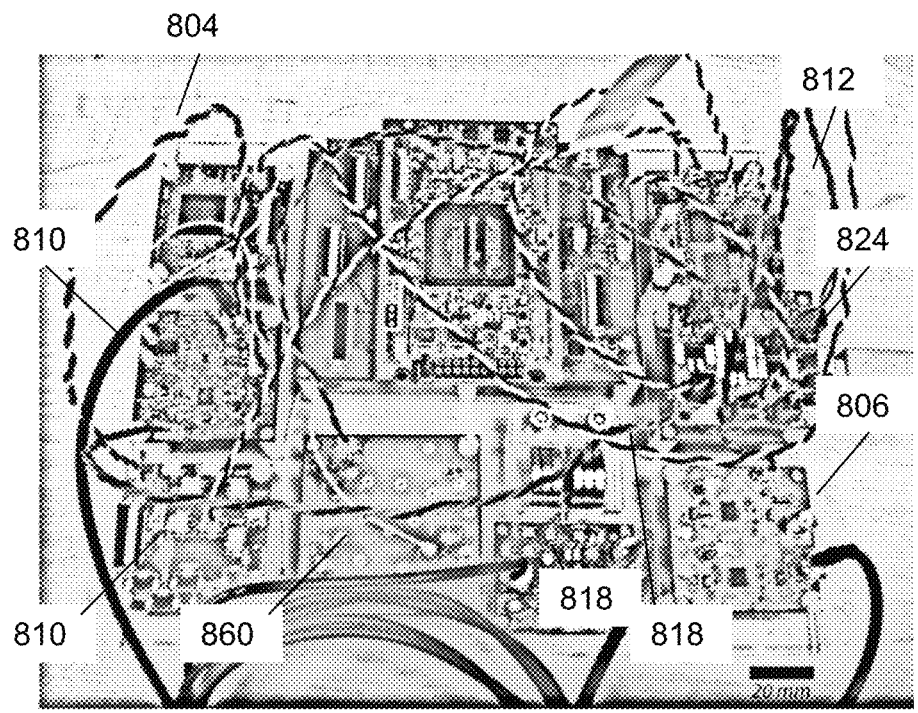
FIG. 8A is a diagram of an entire device in accordance with one aspect of this disclosure.
Figure 8B:
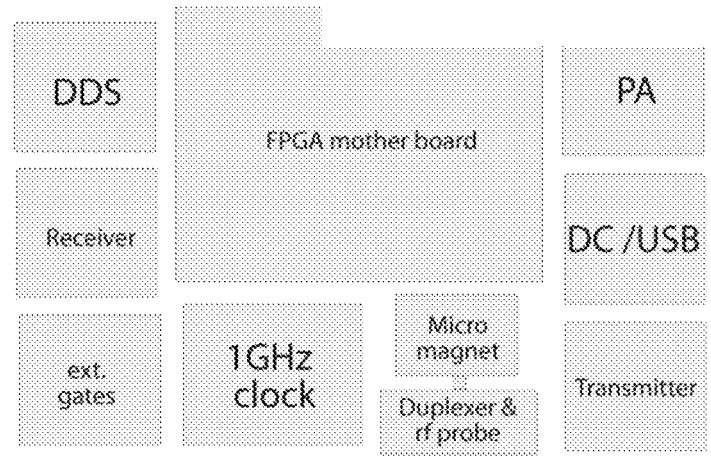
FIG. 8B is a block diagram with corresponding named components for the diagram of FIG. 8A.

FIG. 8A is a diagram of an entire device in accordance with one aspect of this disclosure, and FIG. 8B is a block diagram with corresponding named components for the diagram of FIG. 8A. As identified in FIG. 8B, the device includes a DDS (Direct Digital Synthesis) module 804, a receiver 810, external gates 858, an FPGA mother board 802, 1 GHz clock 860, micro-magnet 818, duplexer and rf-probe 836, power amplifier 812, DC/USB 824 and transmitter 806. The entire system weighs less than 500 g and is developed at a cost of less than $2500.

Figure 9:
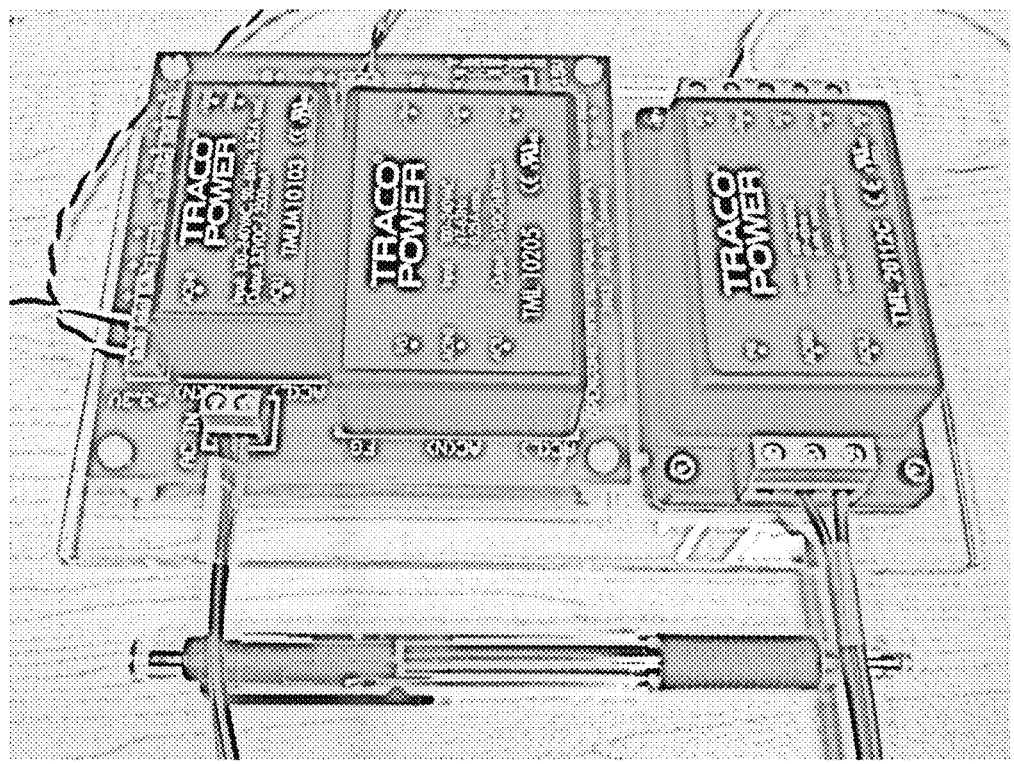
FIG. 9 is a diagram of a power regulator used in accordance with one aspect of this disclosure.

FIG. 9 is a diagram of a power regulator used in accordance with one aspect of this disclosure. In an exemplary embodiment, three dedicated DC-AC converters (TMLM 10103 Traco Power, TML 10205 Traco Power, TML 20112C Traco Power) were used to produce (+3.3 VDC, ±5.0 VDC, 12 VDC) respectively. In an actual device in accordance with one aspect of this disclosure, these converters were mounted separately on an 18 cm by 12 cm acrylic board, which weighs about 450 g. Alternatively, a bulky (a few kilogram) and expensive commercial power supply (e.g., PW8-3ATP, Texio, Japan) which has more advanced functions can be used. As a comparison, a ball-point pen is placed by the side of the system.

Table 1 is a comparison between a magnetic resonance relaxometry device in accordance with one aspect of this disclosure and the state-of-the-art developed by Nan Sun, et al. (see Sun N. et al. Palm NMR and 1-Chip NMR. *Solid State Circuits, IEEE Journal* of 46(1):342-352). The weight does not include the power supplies. As can be seen, one aspect of this disclosure is able to use a re-programmable FPGA processor, has a comparable weight to prior work, is small in size, has a strong magnetic field, has a high power, and obtains a high Q factor of the probe.

TABLE 1

|  | This work | Nan Sun, et al. |
| --- | --- | --- |
| Processor | FPGA | CMOS |
| Weight | 400 g | 100 g |
| Size | 20 cm × 20 cm | Palm-sized |
| Static magnetic field | 0.76 Tesla | 0.5 Tesla |
| Q factor of the probe | 35 | 1.9 |
| Power amplifier | 1000 mWatt | 80 mWatt |

Assembly of the System and MRR Demonstration

Figure 10A:
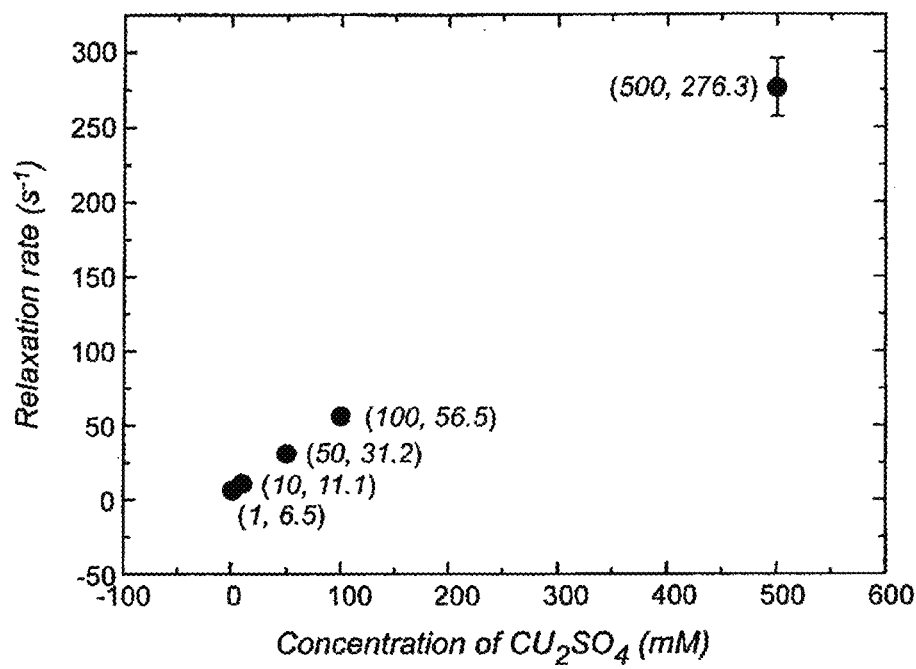
FIG. 10A is a plot depicting the relaxation rate of DI-water doped with $CU_2SO_4$ (in mM concentration), in an experiment in accordance with one aspect of this disclosure.

In an experiment in accordance with one aspect of this disclosure, in order to calibrate the stability and consistency of a homebuilt external magnetic field and rf-probe, the proton relaxation rate of DI-water doped with $CU_2SO_4$ were measured over a large dynamic range of doping concentration (see FIG. 10A). It was demonstrated that the MRR biosensor can be a portable platform for medical diagnosis by measuring the transverse relaxation rate, $R_2$ of actual biological cells. Sodium nitrite, a form of strong oxidant, is toxic to the cells. The experiment showed (FIG. 10B and FIG. 10C) that quick exposure (less than a minute) of whole blood to sodium nitrite will lead to oxidation of the iron heme, from ferrous ($Fe^{2+}$) to ferric ($Fe^{3+}$). This simple redox state, transformed predominantly the oxy-hemoglobin (in healthy whole blood) which is in diamagnetic state into paramagnetic state. This transformation however, increased the bulk magnetic susceptibility of the red blood cells (RBCs) significantly.

150 µL of whole blood taken from healthy donor were exposed to a drop (about 10 µL) of 10 mM of sodium nitrite, $NaNO_2$ (Fluka Analytical, Switzerland) for less than 1 minute. 10 µL, of blood is transferred into microcapillary tube (Drummond Scientific Co.) via capillary action, and then centrifuged at 3000 g for 5 minutes to separate the plasma from the RBCs. The capillary is then loaded into the rf-probe as such that only the RBCs portion is measured. About 350 nL effective volume of RBCs under detection give sufficiently strong echo signal. $^1$H MRR measurements of bulk red blood cells at the resonance frequency of 31.45 MHz inside a micro permanent magnet, $B_o$=0.76 T were performed with Opencore NMR console. The transverse relaxation rates, were measured by standard Carr-Purcell-Meiboom-Gill train pulses (80 µs of inter-echo time) consisting of 2000 echoes, unless mentioned otherwise. All samples were measured at room-temperature. The transmitter power output is maintained at 0.4 W for a single 90°-pulse with pulse length 80 us, which corresponds to a nutation frequency of 3.125 kHz. A recycle delay of 2 s which was set between each pulse is sufficiently long enough to allow all the spins to return to thermal equilibrium.

Figure 10B:
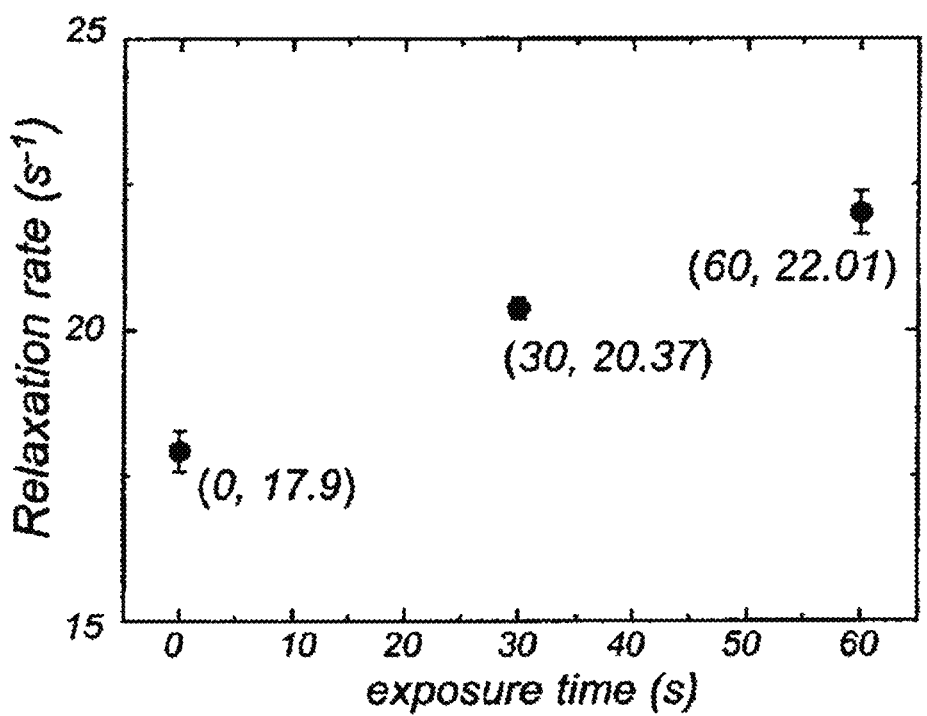
FIG. 10B is a plot depicting proton relaxation rate of RBCs as a function to $NaNO_2$ exposure time (in seconds), in an experiment in accordance with one aspect of this disclosure.
Figure 10C:
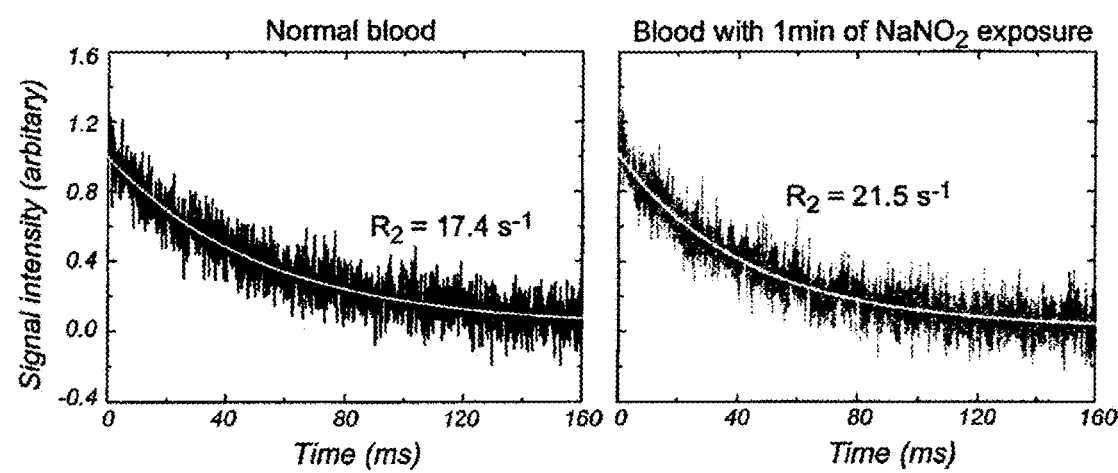
FIG. 10C is a plot depicting the actual echo trains measured for a normal healthy blood (left) and blood exposed to 1 minute of $NaNO_2$, in an experiment in accordance with one aspect of this disclosure.

FIG. 10A is a plot depicting the relaxation rate of DI-water doped with $CU_2SO_4$ (in mM concentration), in an experiment in accordance with one aspect of this disclosure. The parentheses indicate (concentration, relaxation rate). The error bar shown is the standard error measurement (s.e.m.). Note that for lower concentration (100 mM and below) the error bars were relatively too small to be visible in the plot. Parameters used were inter-echo time of 100 µs, 2000 echoes, recycle delay of 2 s and a total of 80 scans were acquired for signal averaging. FIG. 10B is a plot depicting proton relaxation rate of RBCs as a function to $NaNO_2$ exposure time (in seconds), in an experiment in accordance with one aspect of this disclosure. The parentheses indicate (exposure time, relaxation rate). The error bar shown is the standard error measurement (s.e.m). Parameters used were inter-echo time of 80 µs, 2000 echoes, recycle delay of 2 s and a total of 80 scans were acquired for signal averaging. FIG. 10C is a plot depicting the actual echo trains measured for a normal healthy blood (left) and blood exposed to 1 minute of $NaNO_2$, in an experiment in accordance with one aspect of this disclosure.

Major challenges in clinical malaria diagnostics are obtaining sensitive, quantitative results, preferably in a real-time and inexpensive manner. In accordance with one aspect of this disclosure, there is provided a technique for sensitive, quantitative and rapid detection of *Plasmodium falciparum* infected red blood cells (iRBCs), by means of Magnetic Resonance Relaxometry (MRR). During the intra-erythrocytic cycle, malaria parasites catabolize large amount of cellular hemoglobin and convert them into hemozoin crystallites. An embodiment according to one aspect of this disclosure exploits the relatively large paramagnetic susceptibility of these hemozoin particles, which induce substantial changes in the transverse relaxation rate of proton nuclear magnetic resonance of RBCs, to infer the "infection severity" of an infected patient.

In one aspect of this disclosure, the methods discussed may use any of the devices set forth herein, including the hand held or palm size devices discussed above. In some embodiments, the device may be a Nuclear Magnetic Resonance (NMR) device or a Magnetic Resonance Imaging (MRI) device.

In an exemplary embodiment, using an inexpensive bench-top 0.5 Tesla MRR system, with minimal sample preparatory steps and without any chemical or immuno-labeling, a parasitemia level of as low as 0.0002% (<10 iRBCs) in less than 1 µL of whole blood is detected in less than one minute and the entire assay completed in a few minutes. Other devices may be used.

An embodiment according to one aspect of this disclosure is useful for routinely monitoring infections especially in endemic areas (developing countries), or even non-endemic areas (developed countries) whereby trained microscopists are not readily available.

One aspect of this disclosure provides an inexpensive bench-top type MRR system which is capable of rapid detection and quantification of the "parasitemia level," especially in the early stage of infection and classification of stages of infection, in the form of (i) label-free, (ii) artifact-free or less prone to human-error, (iii) minimal sample volume, (vi) minimal sample preparation steps (v) parallel processing, (vi) possibly field-deployable and (vii) low-cost per test.

Figure 11:
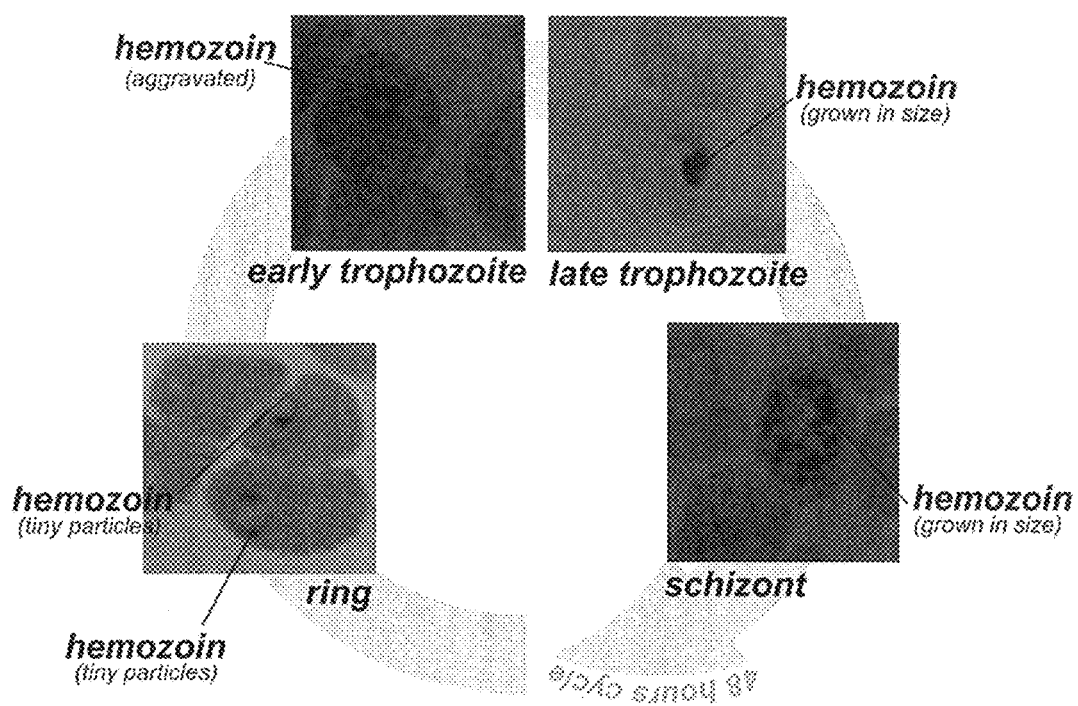
FIG. 11 is a diagram showing the stages of the intra-erythrocytic cycle of malaria parasites.

FIG. 11 is a diagram showing the stages of the intra-erythrocytic cycle of malaria parasites. During infection, malaria parasites penetrate into the host RBCs and use cellular hemoglobin as the main source of amino acids during the 48 hour intra-erythrocytic cycle, in which the iRBCs matures into the three distinct stages known as ring stage, trophozoite and schizont. As the hemoglobin is digested, a large quantity of free heme, which is toxic to cells, is released. In order to protect them from this "self-damaging" reaction, the free heme is immediately converted into an insoluble crystalline known as hemozoin or the "malaria pigment." This pigment is initially deposited inside the vacuoles within the erythrocytes in the ring stage and subsequently becomes more prominent as the cell-cycle proceeds into late stage. Finally, upon rupture of schizont, they are liberated into the bloodstream where they are ultimately scavenged by leucocytes (23, 28, 29). In most clinical cases however, mature parasites (i.e., trophozoite and schizont) are often sequestered in the microcirculation, leaving only immature ring forms in the peripheral circulating blood which is usually sampled for parasitemia assessments.

In FIG. 11, the life cycle of *P. falciparum* is shown during the intra-erythrocytes cycle, indicating the three distinctive stages; ring, trophozoite (early and late), and schizont, as stained with Giemsa-stained blood smear images. Small quantity of hemozoin particles appear as dotted pale yellow pigment inside the vacuoles in the early ring-stage is usually difficult to visualize microscopically. As the parasite matures into subsequent stages, the pigment become more prominent with color ranging from pale yellow to dark brown.

One aspect of this disclosure exploits the presence of the hemozoin crystallites formed within the erythrocyte as early as in the ring stage itself as a natural magnetic label for MRR detection of *P. falciparum* iRBCs. Despite being microscopically small especially in early state of infection (ring-stage), these pigments increase the magnetic susceptibility of RBCs (23, 30), which induces measurable changes in the magnetic resonance relaxation properties of nearby protons (see FIGS. 16A and 16B) (31, 32). With a low cost bench-top 0.5 Tesla MRR and minimal sample preparation procedures (about 3 minutes), an embodiment according to one aspect of this disclosure is able to detect as low as 0.0002% parasitemia (P<0.0003) in about 750 nL of whole blood sample in less than 1 minutes. In experiments, MRR measurements were performed on whole blood spiked with highly-synchronized ring-stage of P. falciparum infected RBCs. In order to mimic the actual peripheral blood sample taken from infected patients, two stages of ring-synchronization were carried out to produce as high as 99.5% purity of ring stage RBCs among the iRBCs. In accordance with one aspect of this disclosure, a new magnetic susceptibility index, based on $R_2$ reading which can potentially assist in classification of severity of infection for clinical prognosis is established. An embodiment according to one aspect of this disclosure may be used to provide (i) a monitoring system, and (ii) a detection system.

Integrated Sample Preparation and Detection

Figure 12:
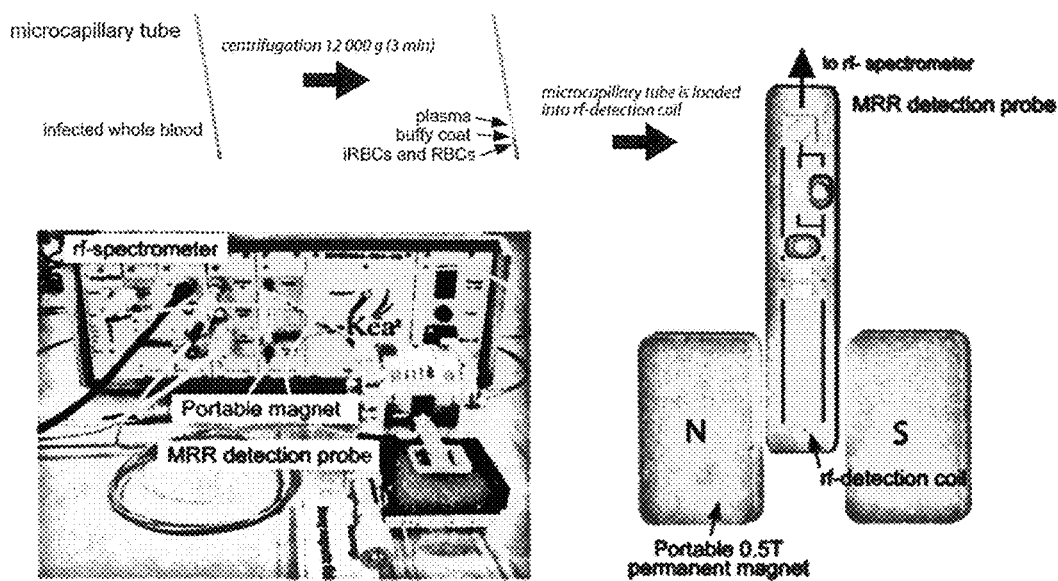
FIG. 12 is a diagram showing steps of sample preparation and detection in accordance with one aspect of this disclosure.
Figure 18:
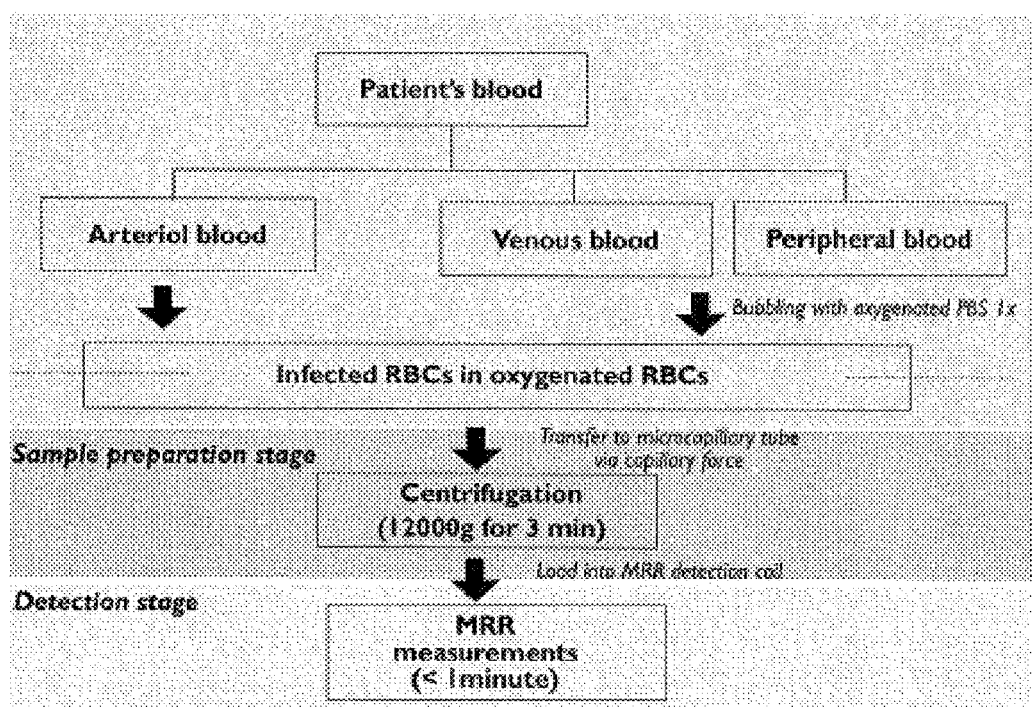
FIG. 18 is a flow chart describing the sample preparation steps to the points of MRR detection for patients' blood samples, in a suggested clinical protocol in accordance with one aspect of this disclosure.

FIG. 12 is a diagram showing steps of sample preparation and detection in accordance with one aspect of this disclosure. Sample preparation steps are minimal, and sample handling is easy and non-laborious. In an example, blood sample from patients (or from culture flasks) is transferred into the microcapillary tube (Drummond Scientific Co.) via capillary action, sealed down with inert plastic adhesive (Sellery Inc.) on one end, and finally spun down in a microcentrifuge (Sorvall Legend Micro 21) at 6000 g for 3 minutes, before slotting them into MRR probe for relaxation measurement (see FIG. 12). Blood sample obtained from peripheral blood or through venepuncture may be bubbled with oxygenated buffer to establish a universal baseline correction for MRR reading (see FIG. 18). Centrifugation allows one to separate and concentrate the RBCs (and iRBCs) from the plasma and buffy coat (PBS or culture media, as in the case of cultured parasites). In order to optimize the MRR signal, only the iRBCs-RBCs pellet (about 300 nL to 500 nL) (31), was placed within the coil's detection region.

In FIG. 12, in accordance with one aspect of this disclosure, there is shown sample preparation using microcapillary tubes. An image (left) is shown of an actual setup which consists of a benchtop rf-spectrometer, portable magnet and rf-detection probe, which compact size make it suitable for laboratories or clinical application. Also shown (right) is a schematic illustration of the MMR detection probe with the electronics and coil integrated on the PCB board. The sample tube is simply slotted into the MMR detection coil.

In accordance with one aspect of this disclosure, the same microcapillary tube used in microcentrifuge is then transferred to MRR detection coil, as shown in FIG. 12. This step obviates the needs to transfer sample from one point to another point, thereby minimizing the chances of sample loss and contamination, and also greatly reduces the processing time. Unlike laborious Giemsa-stained slide preparations and error-prone cell-counting process, the whole assay for MRR, both the sample preparation (3 minutes) and detection stage (less than a minute) is accomplished within 5 minutes. The centrifuge system also allows parallel processing whereby many blood samples can be processed in a single spin.

MRR Detection and Quantification of P. falciparum Infected RBCs

Figure 13:
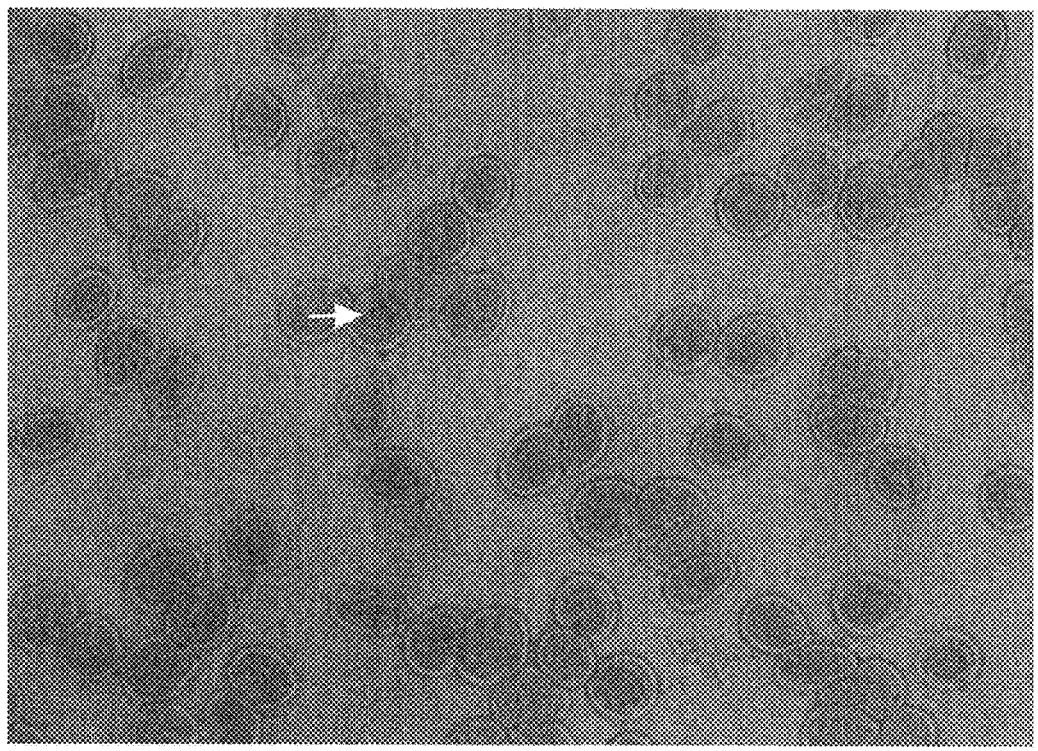
FIG. 13 is an image of Giemsa-stained blood smear microscopy for confirming parasitemia levels of highly synchronized ring-stage infected cells.

In an experiment in accordance with one aspect of this disclosure, the transverse relaxation rates of proton NMR of bulk RBCs spiked with P. falciparum iRBCs, $R_{2(iRBC)}$, were measured for various parasitemia levels (0%, 0.00025%, 0.0005%, 0.001%, 0.0025%, 0.005%, 0.01%, 0.05%, 0.1%, 0.5%, 1%, 5%) prepared through serial dilution with uninfected RBCs obtained from a healthy donor. D-sorbitol treatment was prior performed at the culture stage (32) and magnetic separation (33) was performed to remove almost all the late-stage iRBCs and suspending hemozoin left by the previous generation (see FIG. 17). The parasitemia levels of highly synchronized ring-stage infected cells (92.1%, 7.3%, 0.6%, 0%), denoted as Sample A, were initially confirmed with Giemsa-stained blood smear microscopy (FIG. 13). The parentheses in the foregoing sentence is the short-hand for the breakdown subpopulations of the iRBCs (ring, early trophozoite, late trophozoite, schizont) based on guidelines proposed by World Health Organization (34) (see stages in FIG. 11). FIG. 13 shows an optical microscope image of the Giemsa-stained blood smear showing a 1% parasitemia of highly synchronized ring stage iRBCs. The ring stage iRBC is indicated with arrow.

In an experiment in accordance with one aspect of this disclosure, the transverse relaxation rate of proton NMR of uninfected RBCs, $R_{2(RBC)}$ were measured to establish the baseline to compare the amount of $R_2$ shifted due to the presence of iRBCs.

For a normal healthy person or malaria patients with no other complications, the $R_{2(RBC)}$ reading could differ among individuals. This is due to different fractionation of deoxygenated hemoglobin (deoxy-Hb) and oxygenated hemoglobin (oxy-Hb) (31, 35), which has paramagnetic and diamagnetic susceptibility, respectively. This could create a confounding factor, which may create some individual variation for measured values.

Figure 17:
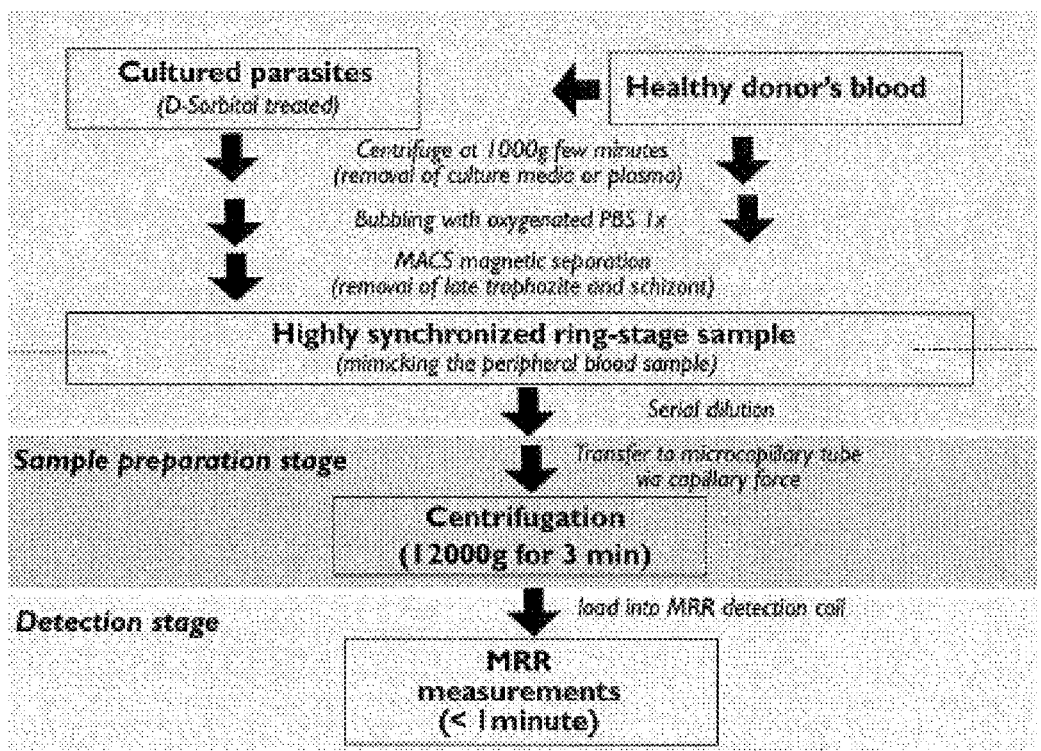
FIG. 17 is a flow chart describing the sample preparation steps to the points of MRR detection for cultured parasites, in an experiment in accordance with one aspect of this disclosure.

In an experiment in accordance with one aspect of this disclosure, in order to suppress or minimize the possible paramagnetic contribution from deoxy-Hb, all of the blood samples were incubated with oxygen-bubbled 1× concentration of phosphate buffered saline (PBS) solution for a few minutes (30) (see below "Methods" section for details and FIG. 17). This converts all the RBCs into oxy-Hb, which is in its diamagnetic states, creating a universal baseline for the measurement.

Figure 19:
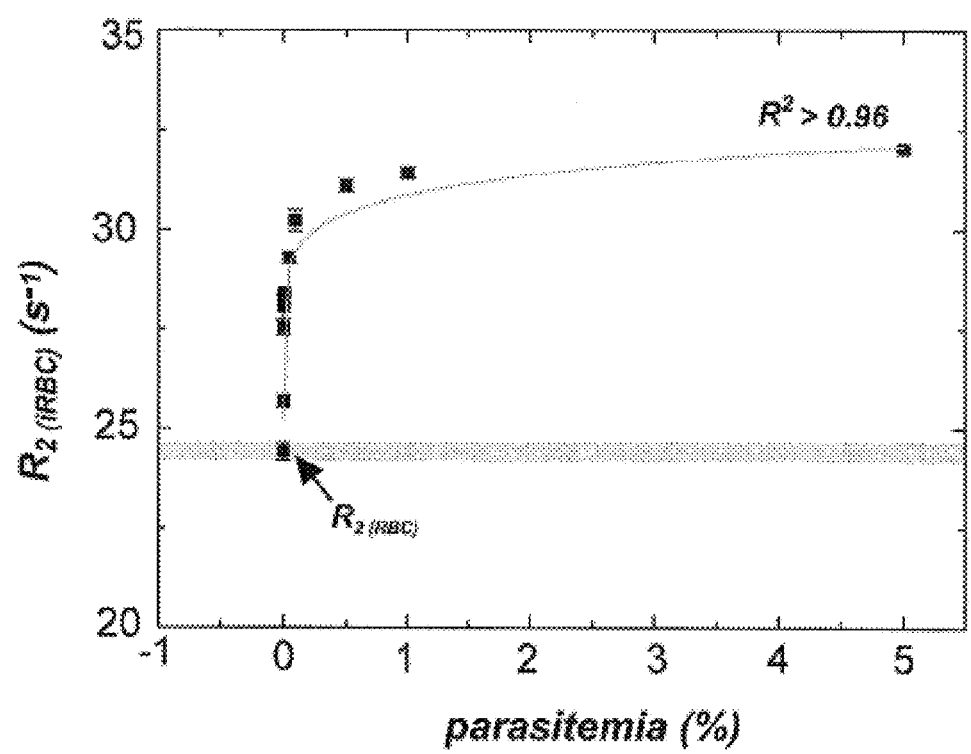
FIG. 19 is a plot of transverse relaxation rate as a function of parasitemia levels for a blood sample, in an experiment in accordance with one aspect of this disclosure.

In the experiment, the $R_{2(iRBC)}$ increases with increasing parasitemia levels as shown in the characteristic curve (see FIG. 19). The increment of the bulk magnetic susceptibilities of the RBCs (as indicated from the enhancement of $R_2$ of the RBCs) was due to the increment of parasitemia (or term as iRBC counts) inside the sample.

Figure 14A:
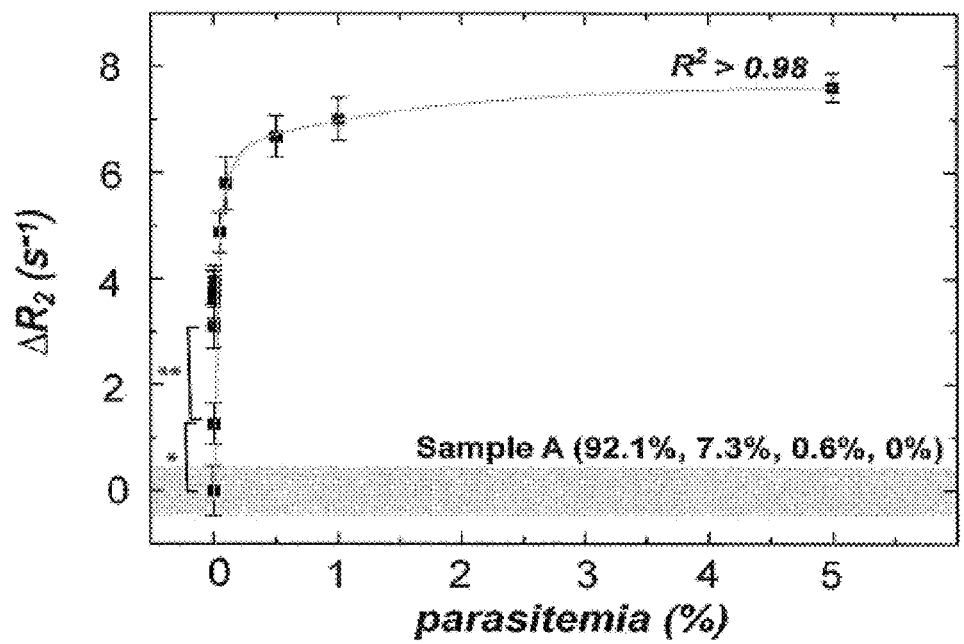
FIGS. 14A, 14B and 15A are plots of enhancement in transverse relaxation rate versus parasitemia levels for three different samples, in an experiment in accordance with one aspect of this disclosure.
Figure 14B:
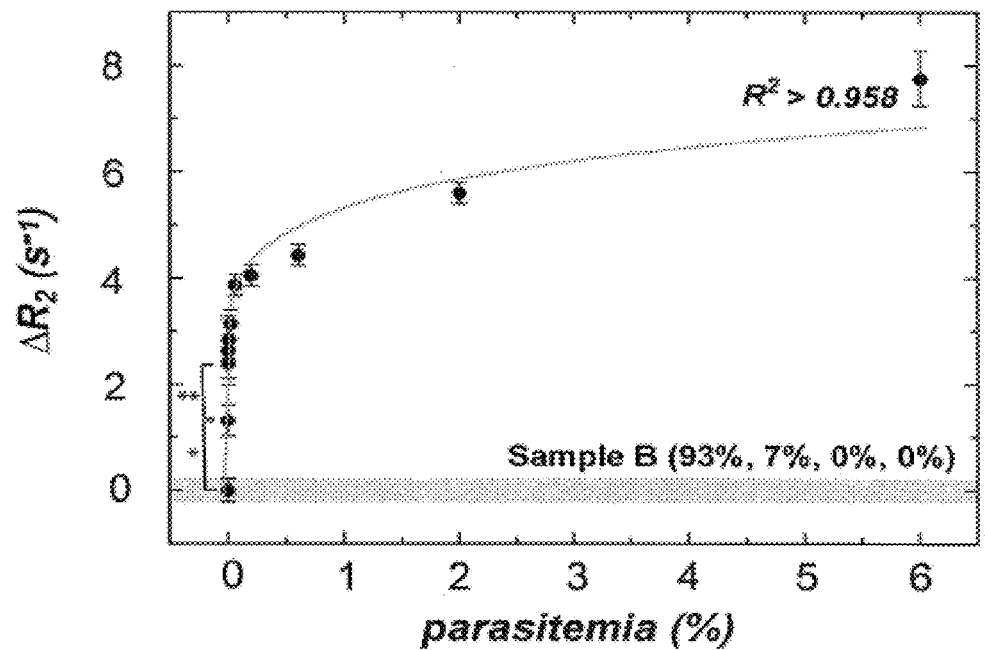
Figure 15A:
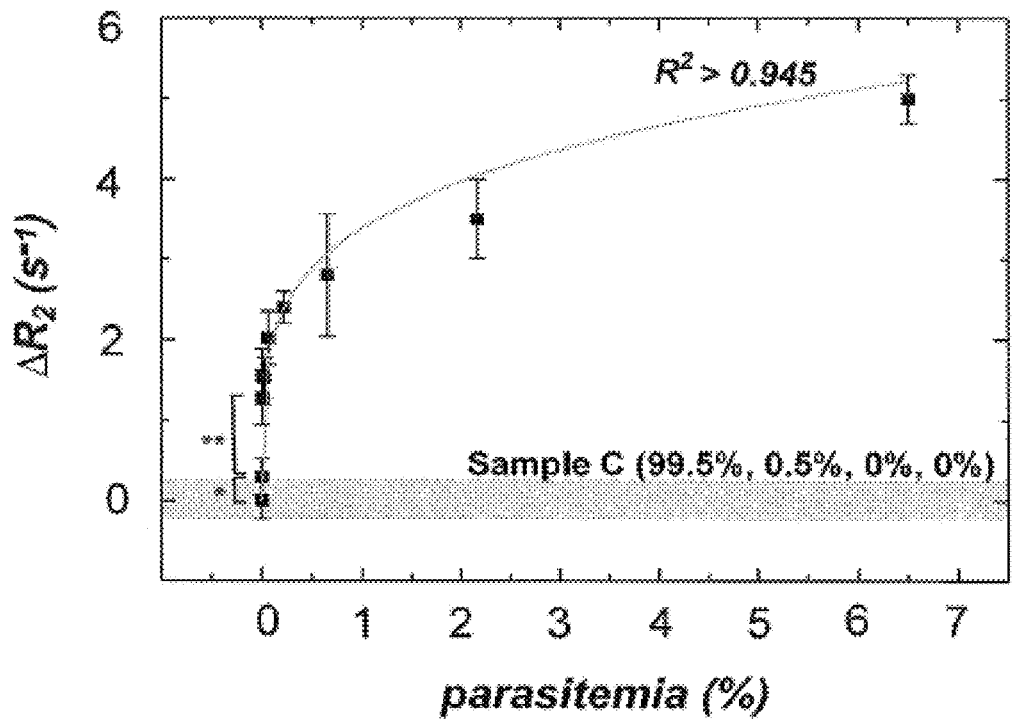
Figure 15B:
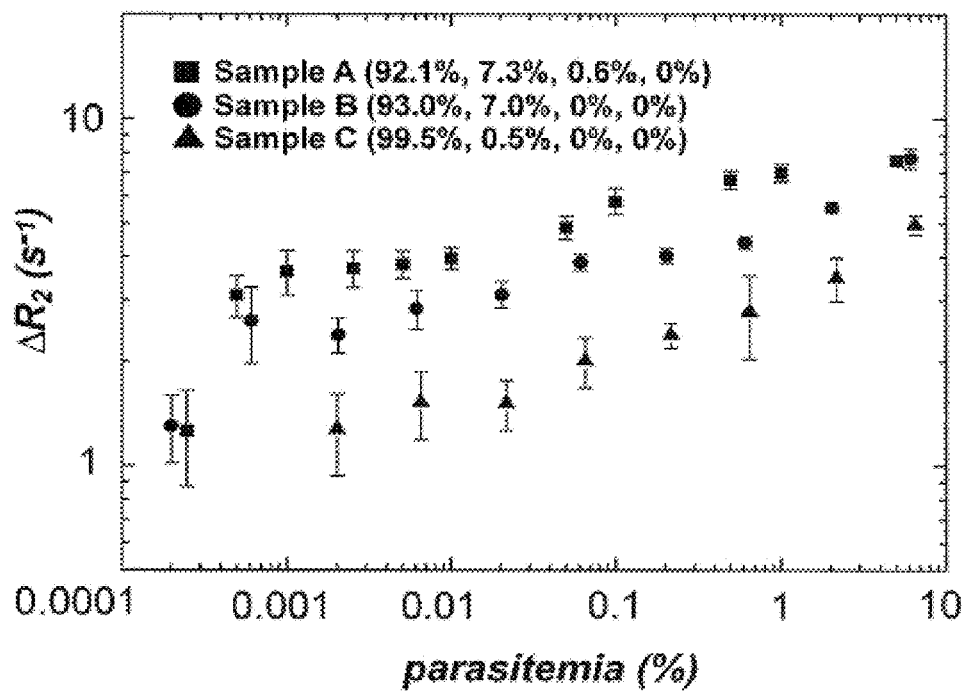
FIG. 15B is a superimposition of the plots of FIGS. 14A, 14B and 15A on a single log-log plot, in an experiment in accordance with one aspect of this disclosure.

FIGS. 14A, 14B and 15A are plots of enhancement of transverse relaxation rate, $\Delta R_2$ as a function of parasitemia levels carried out on three independently cultured parasites (a) blood sample A, (b) blood sample B, (c) blood sample C, spiked with whole blood of three different healthy donors, in the experiment in accordance with one aspect of this disclosure. CPMG echo trains of 60 μs inter-echo times were used. All data are shown in (means±s.e.m). The P-values for the lowest two parasitemia levels for all the sample A, B, C were P<0.05. The uncertainty due to the baseline correction is indicated with grey-bar. The combination of all the plots in log-log format is shown in FIG. 15B.

In the experiment in accordance with one aspect of this disclosure, by calculating the magnitude of the transverse relaxation rate enhanced, $\Delta R_2 = R_{2(iRBC)} - R_{2(RBC)}$, thus a correlation ($R^2 > 0.98$) between $\Delta R_2$ versus parasitemia levels can be established (see FIG. 14A). Such information can be used to assist a clinician to infer the parasitemia level based on $\Delta R_2$-reading.

Also in the experiment, two similar samples (Sample B and Sample C) which consist of higher purity of ring-stage iRBCs Sample B (93%, 7%, 0%, 0%) and Sample C (99.5%, 0.5%, 0%, 0%) were prepared and measured independently. Here, the compositions of trophozoite were reduced to only 7% and 0.5%, respectively. Sample A, B and C gave a good sampling of peripheral blood or venepuncture that is usually obtained clinically (36) has majority of ring-stage iRBCs (75%-99%). In severe malaria cases (33, 37), it is not unusual to find higher load of matured parasites. Despite slightly unique $\Delta R_2$—characteristic curve (see FIG. 14B and FIG. 15A) due to its unique composition of different stages iRBCs, similar trends were observed for Samples B and C respectively, whereby $\Delta R_2$ is an exponentially incremental function of parasitemia level. Significantly, when the 3 graphs were to be superimposed in a single log-log plot (see FIG. 15B), Sample A and Sample B, which contains higher count of trophozoite count than Sample C, has their characteristic curve shifted upwards based on their composition of these mature parasites. This result signifies that, in addition, to the iRBC count, the sub-populations of the various stages of parasites development which has altered the magnetic susceptibilities of the blood is shown and can be measured by MRR. Such quantification based on its parasitemia level as well as the stage of infections can be used to establish "magnetic susceptibility index" to infer the "severity index" for clinical prognosis. Wide dynamic ranges of parasitemia level (FIG. 15B) ranging from the order of 0.00001% to 10% were measured with this technique.

In the experiment, the concentration limit of detection (cLOD) is about 0.0002% (p<0.0003) measured in Sample B. The cLOD is sample-dependent as the sample which contains more mature parasites tends to have higher magnetic susceptibilities and therefore better cLOD can be attained. Sample A recorded to about 0.00025% parasitemia (12.5 iRBCs/μL), which corresponds to roughly less than 10 iRBCs inside the probe (750 nL whole blood or 300 nL of iRBCs which lies which the coil's detection region). Data for parasitemia levels of lower than 0.00025% (p<0.001) were indistinguishable from pure uninfected RBCs. For Sample B and Sample C it was 0.0002% (p<0.0003) and 0.0007% (p<0.05), respectively.

Interpretation of the MRR Signal

One of the major problems in clinical prognosis is to classify the severity of the admitted patients based on parasitemia assessment or clinical symptoms (36,37). Although in general it is acceptable that higher the parasitized iRBC count is, the more severe the infection is. Nevertheless it is also reported that some patients die despite being assessed as low parasitemia level (<0.1%), while some patients are able to walk with 50% of his RBCs parasitized (38). The situation is complicated with some patients may be asymptotic especially at low parasitemia level. This clinical discrepancy is clearly due to the stage and synchronicity of the infection as well as due the "loose relationship" between the peripheral blood-film observed as compared to amount of matured parasites sequestered in microvasculature.

It is clear that a "severity index" is a combined effect of both the parasitemia load, as well as the stage of parasites development from the accurate sampling of blood. As the parasite matures into every stage of the development in its intra-erythrocytic cycle, the pigment grows (see FIG. 11), resulting in higher magnetic susceptibility (30, 39) of the iRBCs. Although skilled microscopists can differentiate the various parasite stages, they are limited in their ability to quantify them in consistent and comparable manner. For example, there is currently no consistent way to classify early stage of ring and a late stage of ring, or many other borderline cases.

In accordance with one aspect of this disclosure, such shortcomings can be addressed by classifying these iRBCs based on a "magnetic susceptibility index" (see FIG. 15B). It proves valuable in quantifying (with higher accuracy) the level of infection. While subject to future clinical validation, we believe such information is likely to improve diagnosis and for clinicians to judge the patients' condition.

For example, as one illustration of establishing a magnetic susceptibility index, a measurement could be made of change in transverse relaxation rate of the concentrated red blood cells relative to a predetermined standard for transverse relaxation rate for blood that is not infected with a disease. With reference to FIG. 15B, it can be seen that one could use the change in transverse relaxation rate, $\Delta R_2$, to determine likelihoods of the patient having certain parasitemia levels and certain stages of infection. A magnetic susceptibility index could be determined, corresponding to the measured change in transverse relaxation rate, each level of which magnetic susceptibility index could be associated with likelihoods of the patient having certain parasitemia levels and certain stages of infection. In one embodiment, the magnetic susceptibility index can be the change in transverse relaxation rate itself; in other embodiments, the magnetic susceptibility index can be a different number determined based on the change in transverse relaxation rate. In an embodiment according to one aspect of this disclosure, the magnetic susceptibility index may be used as an indication of whether a patient is infected with a disease (a "yes" or "no" decision), which is particularly useful at very low parasitemia levels.

More generally, as used herein, determining a "magnetic susceptibility index" may include determining an index related to parasitemia level and stage of infection, in cells from an animal body, based at least in part on a measured transverse relaxation rate. The "magnetic susceptibility index" may be used to infer a "severity index" for clinical prognosis.

As used herein, a determination of an "infection level" may include one or more of determining a parasitemia level, a stage of infection, and/or a magnetic susceptibility index.

According to one aspect of this disclosure, methods and devices discussed herein may be used to study the in-vitro or in-vivo activity or metabolism of microbes, bacteria or other micro-organisms.

According to a further aspect of this disclosure, methods and devices discussed herein may also be used to perform micro-imaging, for example (but not limited to) micro-imaging of items such as a strand of hair, a strand of silk or other items.

According to a further aspect of this disclosure, methods and devices discussed herein may also be used as a generic platform to gauge the amount of oxidative stress or stress level on a certain individual.

According a further aspect of this disclosure, methods and devices discussed herein may also be used for the diagnosis of any disease (provided that the biomarkers can be uncovered by means of magnetic resonance), or immuno-labeling, within a single portable system.

Portions of the above-described embodiments can be implemented using one or more computer systems. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

In addition, as used herein, determination of an "infection level" based on a "transverse relaxation rate," determining a "magnetic susceptibility index," other calculations, quantities, variables and determinations and/or other portions of the embodiments herein may be performed and/or embodied in electronics in digital media.

In this respect, at least a portion of an embodiment according to one or more aspects of this disclosure may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments according to aspects of this disclosure discussed above. The computer readable medium or media can be transportable, such that the program or programs stored thereon can be loaded onto one or more different computers or other processors to implement various aspects of this disclosure as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Clinical Application

Two possible modes of clinical operations can potentially be used based on MRR detection in accordance with an aspect of this disclosure: (i) 'detect-to-monitor' and (ii) 'detect-to-identify.' In most hospitals, monitoring patients' relapse (e.g. drug therapy assessment) is not uncommon and in fact inevitable. Assuming that there is no other complication that contributes drastically to the changes of $R_2$, therefore any fluctuations of $R_2$ can be attributed to the presence of parasites. By measuring the fluctuation $\Delta R_2$ over a period of time, MRR can give a quick assessment of the patient's condition based on the severity index. MRR which has good sensitivity (or good resolution), coupled with minimal sample preparation and very low cost per test, makes MRR an excellent tool for routine job like monitoring a patient's condition.

It is worth noting that absolute value of $R_{2(iRBC)}$ taken from an infected patient may not be directly comparable among another patient due to human-to-human variations (e.g. natural level of methemoglobin in our body, RBCs' life-cycle, etc). From our experience in an experiment in accordance with one aspect of this disclosure, $R_{2(RBC)}$ obtained from healthy donors may differ as much as 0.4 ms despite being prepared in exactly the same procedure, which may render the lower detection limit to about 0.001% or lower. Considering that a patient is only likely to show symptom at parasitemia level of 0.002% (40), therefore it is not a limiting factor. Nevertheless, this sensitivity level is still comparable to the state-of-the-art Giemsa-stained microscopy.

In order to establish a detect-to-identify in accordance with one aspect of this disclosure, it is likely that an internal reference value $R_{2(RBC)}$ of uninfected RBCs of the patient himself has to be known beforehand. However, $R_{2(RBC)}$ of uninfected blood is not readily available when the patient is infected. One elegant way to overcame this problem, in accordance with one aspect of this disclosure, is to compare the two $R_{2(iRBC)}$ readings taken in a span of time. Should the patient be healthy there should be no substantial changes in $R_2$ reading, assuming that there is no other complications. Should the patient be infected, there will be a spike change in $R_2$ reading given that MRR has sensitivity of about 0.0005%. There are however many existing techniques such as gradient centrifuge (41), or margination effect (42) which can isolate the uninfected RBCs from the infected RBCs (currently work under progress). Nonetheless, with more advanced radio-frequency pulse sequences (e.g. 2D NMR), more specific information (e.g. structural protein, binding sites, diffusion) can be revealed (43). Alternatively, microscopy technique may be incorporated in addition to MRR measurement for confirmation test. For monitoring system, $R_{2(RBC)}$ baseline reading is not required since the comparison is based on his/her reading himself.

Detection Sensitivity and Merits of MRR

The cLOD of an MRR system in an experiment in accordance with one aspect of this disclosure (0.0002%) is much higher than Giemsa-stained microscopy (0.001%) and comparable to PCR-technique (0.0001%). Using a thick blood film, a well-trained microscopist can identify 0.001% parasitemia (about 50 parasites/μL of blood). Most routine diagnostics in laboratory, however, generally achieve much lower sensitivity of about 0.01% of parasitemia (18). Thin film smears, which gives better visualization of the parasites, generally have only 1/10 sensitivity of thick film (17). When slides are examined by technicians who are not specifically trained for malaria diagnosis, sensitivity is much lower with parasitemia level of <0.01% not detected even after 10 minutes of examination (44). Unfortunately, majority of the malaria cases occurs in poor countries where trained technician are becoming rare. Moreover, microscopy technique, despite being the 'gold-standard', has an accuracy of only 70%-75% due to human errors (19, 45). Human errors appear in many forms such as miscalculation, difficulty to identify early ring stage, misinterpretation due to artifacts from the stain or lack of experience. Misdiagnosis can leads to improper treatment and in severe cases prove fatal.

Another major issue in malaria diagnosis is to provide rapid diagnosis to warrant timely therapy. Early therapy facilitates better drug management and thus reduces morbidity and mortality. Generally in hospital, microscopic-based assay from finger prick to the point when result is released requires more than 40 minutes to about an hour. Samples of very low parasitemia level or negative confirmation test require even longer inspection time. Rapid detection minimizes the gap between sample collection and measurement, thus avoiding substantial changes in the parasite load. Despite the need to have highly sensitive diagnostics for confirmation test, on the other hand, a single negative result does not automatically rule out malaria infection. More often than not, decades of past experience has taught practitioners to instead, do a continuous monitoring and diagnosis over a period of 48 hours for patients who show malaria symptoms (23). It is therefore, highly desirable to be able to do continuous, reliable and rapid parasitemia check without tedious sample preparation steps.

Notably, with minimal sample preparation, MRR in accordance with one aspect of this disclosure is able to detect in almost real-time mode (about 1 minutes) in <1 µL of whole blood with high sensitivity. In contrast rapid diagnostic kit is species-specific (46) and does not provide quantitative information on the density of parasites (19), we expect the MRR in accordance with one aspect of this disclosure to also work on less infectious and less common human infecting parasites such as $P.$ $malariae$, $P.$ $vivax$, and $P.$ $ovale$, since hemozoin is a common signature among hemoglobin-feeding parasites (47), although further studies on the magnetic susceptibility index of each respective parasites may be necessary. In this sense, it is also advantageous to use MRR in accordance with one aspect of this disclosure in cases where mixed infection may occur.

The high volume sensitivity of MRR in accordance with one aspect of this disclosure can be attributed to the micron-sized radio-frequency (rf) detection coil, which produces strong magnetic fields per unit current (48), and the centrifugation technique which purifies (separates and concentrates) the RBCs from the plasma, resulting in higher sample stability and consistency in MRR measurements. Since MRR has high accuracy and consistency and does not rely on human subjective judgment, it can be a valuable tool for routine quick parasitemia level check for already infected patient, and for monitoring malaria recurrence. Human errors in manual cell counting as in the case of microscopy technique should be greatly reduced, and the over-reliance on well-trained technician can be lifted off (18). The ability of MRR to handle and detect small sample volume allows one to concentrate the parasitemia to a greater level. Typically, a finger prick from an infected patient gives about 20-30 µL of whole blood, and thus very low parasitemia (e.g. 0.0001%) samples can be concentrated by using existing separation-concentration techniques (41, 42). Using a pre-concentration technique of e.g. 10× enrichment, a smaller sample volume of higher parasitemia (e.g. 0.001% in 3 µL) can be obtained; well within the detection limit of an MRR setup in an experiment in accordance with one aspect of this disclosure. Implementing and integrating these existing concentration techniques into MRR systems in accordance with one aspect of this disclosure will further enhance the cLOD of MRR while leveraging its rapid detection capabilities. The electronics can be packaged onto a single chip and pre-programmed with user-friendly radio-frequency pulse sequences in efforts to make cheaper and easier to use point-of-care like MRR systems (26, 49). Although the cost of MRR instrumentation may be expensive for malaria-endemic countries, the cost per test is extremely low. Only a haematrocrit tube and PBS-reagent is needed, which cost far less than a dollar, as compared to PCR ($3), and dipsticks ($3-$10) (40).

Reliability and Consistency of MRR Measurements

Figure 20:
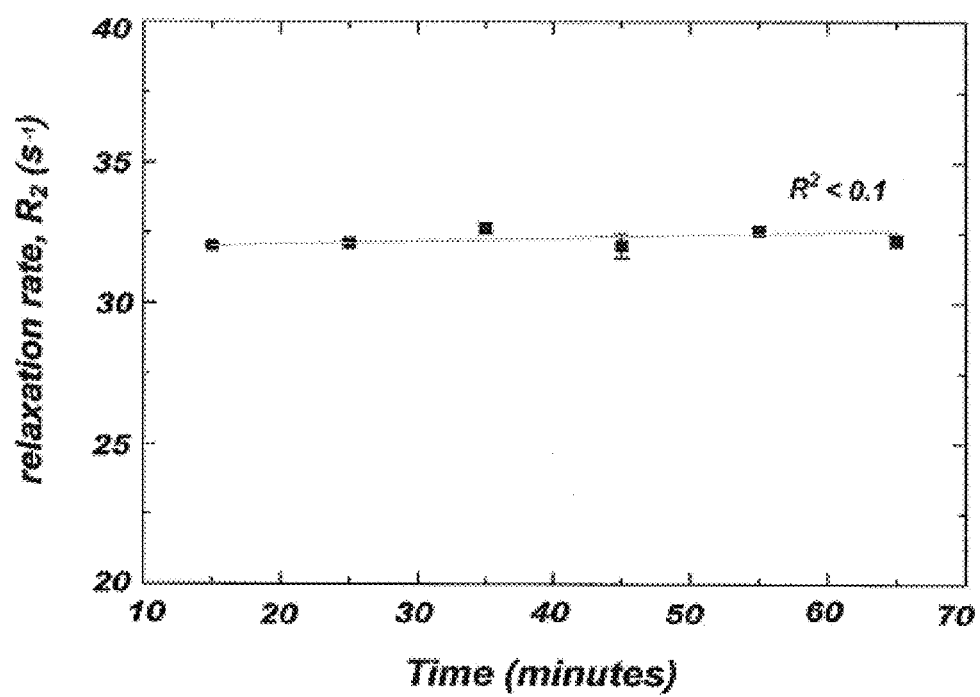
FIG. 20 is a plot of transverse relaxation rate of infected red blood cells measured over a period of one hour to evaluate drift over time, in an experiment in accordance with one aspect of this disclosure.

In order to evaluate the consistency and reliability of this technique, MRR measurements for 5% parasitemia were carried out continuously over a period of one hour, in an experiment in accordance with one aspect of this disclosure. Although there is a slight time-drift in $R_{2(iRBC)}$ but it is not significant ($R^2<0.1$) as depicted in FIG. 20. This indicates high level of reproducibility and accuracy of MRR measurement. This is probably due to the fact that for the ring-stage there is no substantial change in the quantity of iRBCs inside the measured sample within the measurement time frame.

Conclusion

In accordance with one aspect of this disclosure, it has been demonstrated that the paramagnetic nature of the tiny fraction of hemozoin which are present as early as the ring-stage in iRBCs during malaria infection can be used as a natural biomarker for disease diagnostic. Classification via "magnetic susceptibility index" measured with MRR technique correlates well with "severity index," and can be a valuable means for clinical prognosis, drugs prescription, hospitalization criteria, moderate or severe zone and so forth. An MRR assay in an experiment in accordance with one aspect of this disclosure, despite not being optimized for clinical application, offers comparable (if not higher) sensitivity to other traditional malaria diagnosis methods or PCR technique. By integrating pre-enrichment techniques and by employing higher magnetic field, MRR in accordance with one aspect of this disclosure would produce much higher sensitivity than current state-of-the-art PCR, which exploits DNA amplifications. MRR measurement in accordance with one aspect of this disclosure provides higher accuracy (less prone to human error, and artifacts free), rapid and yet quantitative diagnosis in an inexpensive manner and offers an attractive alternative to traditional Giemsa-blood smear microscopy and dipsticks. Due to MRR's ability to provide 'non-invasive' (without having to lyse the cells) information in almost real-time mode, an embodiment according to one aspect of this disclosure may have significant impact on metabolomic studies of cells and tissues.

A discussion of experiments in accordance with one aspect of this disclosure follows:

Methods

Magnetic Resonance Relaxation Measurement and Detection.

$^1H$ MRR measurements of bulk red blood cells at the resonance frequency of 21.65 MHz (see FIG. 21B) inside a portable permanent magnet (Metrolab Instruments, Switzerland), $B_o=0.5$ T were performed with bench-top type console (Kea Magritek, New Zealand). Single resonance proton MRR probe with detection coil of 900 µm inner diameter was constructed to accommodate MRR sample microcapillary tube (o.d: 900 µm, i.d.: 550 µm) (Drummond Scientific Co., Broomall, Pa.) for a detection region of approximately 300 nL. The electronic parts and coil were mounted on a single printed circuit board (FIG. 12). The transverse relaxation rates, $R_2$ were measured by standard Carr-Purcell-Meiboom-Gill train pulses (60 µs of inter-echo time) consisting of 5000 echoes. A total of 48 scans were typically acquired for signal averaging unless mentioned otherwise. All samples were measured at room-temperature. All data were acquired five times and reported as (means±standard error measurement (s.e.m)). The transmitter power output is maintained at 1.56 W for a single 90°-pulse of pulse length 14 us, which correspond to nutation frequency of 17.9 kHz. A recycle delay of 1 s which was set between each pulse is sufficiently long enough to allow all the spins to return to thermal equilibrium. For experiments with magnetic beads suspended in DI-water, longer recycle delay of 30 s were used.

Cell-Culture of *P. falciparum*.

*P. falciparum* 3D7 strain was used in this study. Parasites were cultured in RPMI medium 1640 (Invitrogen, USA) supplemented with 0.3 g of L-glutamine, 5 g of AlbuMAX II (Invitrogen, USA), 2 g NaHCO3, and 0.05 g of hypoxanthine (Sigma-Aldrich, USA) dissolved in 1 mL of 1 M NaOH, together with 1 mL 10 mg/mL of Gentamicin (Invitrogen, USA). Parasites were synchronized at ring stage using 2.5% D-sorbitol to maintain a synchronous culture. Cultures were stored at 37° C. after gassing with a 5% CO2, 3% O2 and 92% N2 gas mixture and their hematocrit maintained at 2.5%. Highly synchronized ring stage iRBCs (more than 90%) were harvested. Whole blood for parasite culture was obtained from healthy donors and was spun down to separate the RBCs. The RBC pellet was treated with citrate phosphate dextrose adenine (CPDA) for 3 days before being washed three times with RPMI 1640 and stored for use.

Preparation of *P. falciparum* iRBCs and Sample Dilution.

*P. falciparum* infected RBCs of 10.0% parasitemia level were obtained from cultured parasites, as described above. These iRBCs were then spun down in a microcentrifuge (Sorvall Legend Micro 21) at 1000 g for about 3 minutes, washed three times with isotonic PBS solution, and resuspend them in PBS solution for 10 minutes. The PBS solution was previously bubbled with ambient air for a few minutes so that all the hemoglobin will be converted into oxyhemoglobin states (30). Sample of various parasitemia level were prepared by spiking iRBCs into uninfected RBCs and subsequently diluted to various parasitemia levels ranging from 0.0002% to 6.5%.

Magnetic Separation.

The cultured-parasites which consist of highly purified ring stage were further purified (33) with MACS system (25 LD columns, Miltenyi Biotec, Germany). The LD columns were preloaded with rinsing buffer (0.5% BSA in 1×PBS), which was held with Quadro MACS magnetic support. The blood was then passed through the column. The non-magnetic parts (uninfected RBCs) and low magnetic susceptibility especially the ring-stage will be able to pass through the column without being trapped. Most of the late stage (trophozoite and schizont) and suspending hemozoin from the previous generation will be trapped inside the column.

Additional Methods.

Details on an electrical circuit, other experimental protocols and a suggested clinical protocol, in accordance with one aspect of this disclosure, are included below.

1. Proof of Concept: Effect of Superparamagnetic Beads on the Transverse Relaxation Rates of Proton Spins in DI-Water.

Figure 16A:
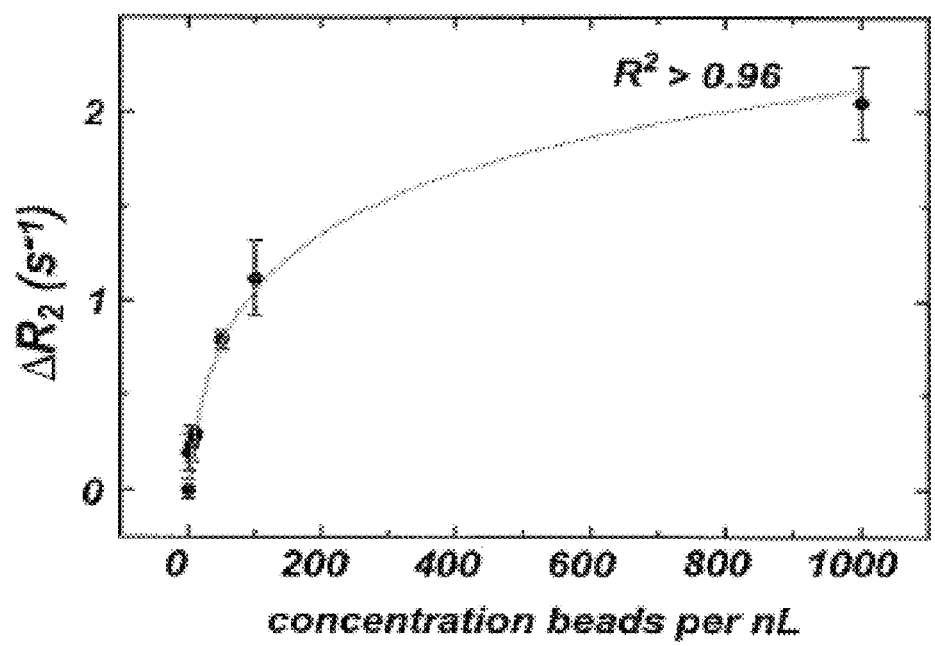
FIG. 16A is a plot of enhancement of transverse relaxation rate of de-ionized water as a function of various concentrations of super paramagnetic beads.
Figure 16B:
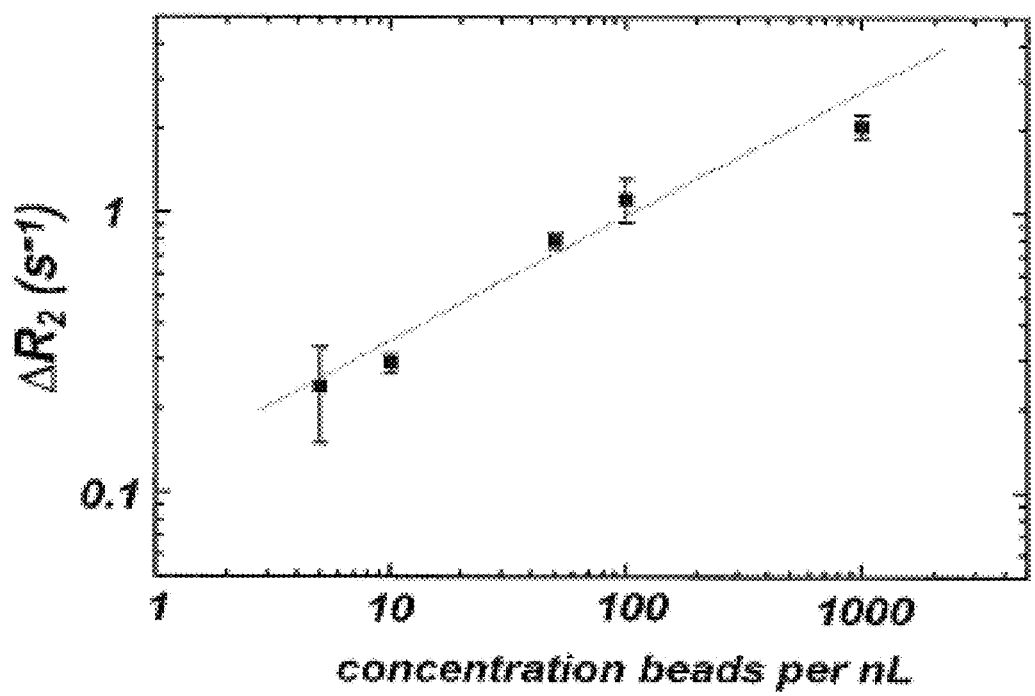
FIG. 16B is a log-log plot of the same, in an experiment in accordance with one aspect of this disclosure.

As proof of concept, the effect of the concentration of superparamagnetic beads on the transverse relaxation rates of proton spins in DI-water, $R_2$ were studied. As depicted in FIGS. 16A and 16B, as the concentration of the beads were increased ($R^2 > 0.985$), the overall magnetic susceptibility of the beads increases, which in return enhanced the $R_2$ of the DI-water. Using the same principle, the concentrations of the hemozoin which is paramagnetic in nature are able to induce measurable changes in the transverse relaxation rate of proton NMR in blood.

Sample Preparation for MRR Detection of Superparamagnetic Beads.

Magnetic beads (Anti-Biotin MACSi Beads) of approximately 3.5 µm were purchased from Miltenyi Biotec GmbH. A stock solution of 1000 beads per nL were prepared by spiking the beads into DI-water and subsequently diluted into various concentrations (0, 5, 10, 50, 1000 beads per nL respectively). Microcapillary tube was used to transfer the diluted beads through capillary force and one end of the tube was sealed off with plastic adhesive.

FIGS. 16A and 16B

Plot for enhancement of transverse relaxation rate, $\Delta R_2$ of DI-water as a function for various concentrations of super paramagnetic beads (FIG. 16A). CPMG train echoes at echo interval of 50 µs were used. A total of 80 scans were acquired and a recycle delay of 30 s was used between each scans. Shorter recycle delays were used for experiments with higher beads concentration. All data are shown in (means f s.e.m). Log-log plot is shown in FIG. 16B. A line was drawn as a guideline to the eye.

2. Experimental Procedure

FIG. 17

In order to mimic the clinical blood sample obtained from patients (blue box), two stages of purification (D-Sorbitol and MACS) were carried out to harvest highly-synchronized ring-stage sample. A flow chart describing the sample preparation steps (green box) to the points of MRR detection (yellow box) for cultured parasites. The same protocols were applied to all three samples A, B, and C.

3. Suggested Protocol for Clinical Sample.

FIG. 18

A flow chart describing the sample preparation steps to the points of MRR detection for patients' blood samples. Blood taken via venepuncture or peripheral blood which contain an unknown fraction of de-oxygenated Hb will have to be bubbled with oxygenated PBS in order to obtain universal baseline for MRR measurement.

4. Transverse Relaxation Rate, $R_{2(iRBC)}$ as a Function of Parasitemia Levels for Blood Sample A.

FIG. 19

Plots of transverse relaxation rate, $R_{2(iRBC)}$ as a function of parasitemia levels for blood sample A. CPMG echo trains of 60 µs inter-echo times were used. All data are shown in (means±s.e.m). The $R_2$ of uninfected RBCs (at 0% parasitemia), $R_{2(RBC)}$ is indicated. The uncertainty due to the baseline correction is indicated with grey-bar.

5. Sample Stability and Time-Drift Measurement.

FIG. 20

Transverse relaxation rate of iRBCs measured with CPMG train echoes at inter-echo time of 60 µs acquired over a period of one hour to evaluate its drift over time. Sample used were 5% parasitemia of Sample A.

6. Electrical Circuit and Impedance Matching of the Coils.

Figure 21A:
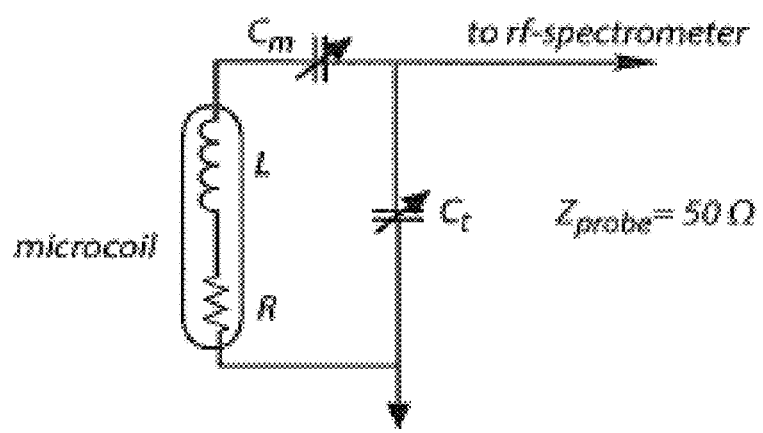
FIG. 21A is a schematic diagram of an electrical circuit of an NMR rf-probe used in an experiment in accordance with one aspect of this disclosure.
Figure 21B:
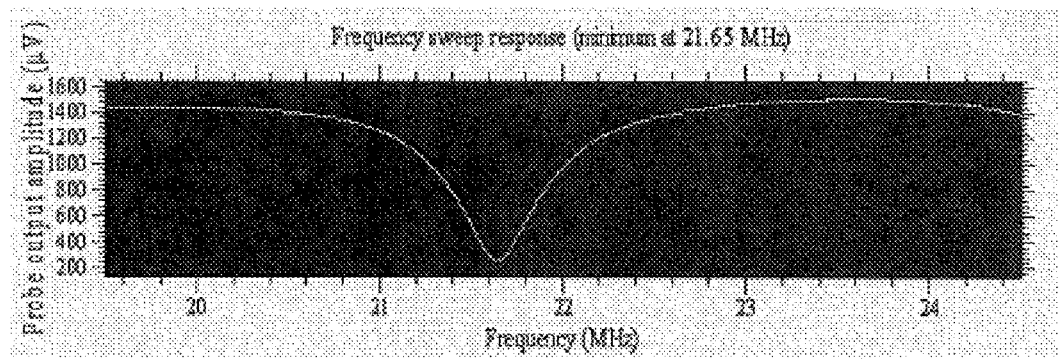
FIG. 21B is a plot of frequency sweep response for the electrical circuit of FIG. 21A.

FIGS. 21A and 21B

Schematic diagram (FIG. 21A) of the electrical circuit of NMR rf-probe with impedance of the microcoil was tuned to 50Ω at 21.65 MHz (FIG. 21B), by using the variable capacitance at $C_t$~68 pF and $C_m$~1400 pF.

7. Competitive Edges of MRR as Compared to Existing Technologies

FIG. 22

FIG. 22 is a table showing competitive advantageous of MRR as compared to existing technologies such as microscopy, PCR, and dipstick.

REFERENCES

1. Lee H, Sun E, Ham D, & Weissleder R (2008) Chip—NMR biosensor for detection and molecular analysis of cells. *Nature medicine* 14(8):869-874.
2. Lee H, Yoon T, Figueiredo J, Swirski F, & Weissleder R (2009) Rapid detection and profiling of cancer cells in fine-needle aspirates. *Proceedings of the National Academy of Sciences* 106(30):12459.
3. Liu Y, Sun N, Lee H, Weissleder R, & Ham D (2009) CMOS mini nuclear magnetic resonance system and its application for biomolecular sensing. (IEEE), pp 140-602.
4. Sun N, Liu Y, Lee H, Weissleder R, & Ham D (2009) CMOS RF Biosensor Utilizing Nuclear Magnetic Resonance. *Solid-State Circuits, IEEE Journal of* 44(5):1629-1643.
5. Sun N, et al. (Palm NMR and one-chip NMR. (IEEE), pp 488-489.
6. Casanova F, Danieli E, Perlo J, & Blumich B (2010) Small Magnets for Portable NMR Spectrometers. (Translated from English) *Angewandte Chemie-International Edition* 49(24):4133-4135 (in English).
7. Blumich B, et al. (1998) The NMR-mouse: construction, excitation, and applications. (Translated from eng) *Magn Reson Imaging* 16(5-6):479-484 (in eng).
8. Demas V, et al. (2007) Portable, low-cost NMR with laser-lathe lithography produced microcoils. (Translated from eng) *J Magn Reson* 189(1):121-129 (in eng).
9. Sillerud L, et al. (2006) 1H NMR Detection of superparamagnetic nanoparticles at 1 T using a microcoil and novel tuning circuit. *Journal of Magnetic Resonance* 181(2):181-190.
10. Sun N, et al. (Palm NMR and 1-Chip NMR. *Solid-State Circuits, IEEE Journal of* 46(1):342-352.
11. Takeda K (2007) A highly integrated FPGA-based nuclear magnetic resonance spectrometer. (Translated from eng) *Rev Sci Instrum* 78(3):033103 (in eng).
12. Takeda K (2008) OPENCORE NMR: open-source core modules for implementing an integrated FPGA-based NMR spectrometer. *Journal of Magnetic Resonance* 192 (2):218-229.
13. Mclachlan L A (1980) Lumped Circuit Duplexer for a Pulsed Nmr Spectrometer. (Translated from English) *Journal of Magnetic Resonance* 39(1):11-15 (in English).
14. Massin C, et al. (2002) High-Q factor RF planar microcoils for micro-scale NMR spectroscopy. (Translated from English) *Sensors and Actuators a-Physical* 97-8: 280-288 (in. English).
15. Massin C, et al. (2003) Planar microcoil-based microfluidic NMR probes. (Translated from English) *Journal of Magnetic Resonance* 164(2):242-255 (in English).
16. Snow R, Guerra C, Noor A, Myint H, & Hay S (2005) The global distribution of clinical episodes of *Plasmodium falciparum* malaria. *Nature* 434(7030):214-217.
17. Warhurst D C & Williams J E (1996) ACP Broadsheet no 148. July 1996. Laboratory diagnosis of malaria. (Translated from eng) *J Clin Pathol* 49(7):533-538 (in eng).
18. Moody A (2002) Rapid diagnostic tests for malaria parasites. (Translated from eng) *Clin Microbiol Rev* 15(1):66-78 (in eng).
19. Amexo M, Tolhurst Re, Brackish G, & Bates I (2004) Malaria misdiagnosis: effects on the poor and vulnerable. (Translated from eng) *Lancet* 364(9448):1896-1898 (in eng).
20. Caramello P, Lucchini A, Savoia D, & Gioannini P (1993) Rapid diagnosis of malaria by use of fluorescent probes. (Translated from eng) *Diagn Microbiol Infect Dis* 17(4):293-297 (in eng).
21. Snounou G, Viriyakosol S, Jarra W, Thaithong S, & Brown K N (1993) Identification of the four human malaria parasite species in field samples by the polymerase chain reaction and detection of a high prevalence of mixed infections. (Translated from eng) *Mol Biochem Parasitol* 58(2):283-292 (in eng).
22. Plowe C V (2005) Antimalarial drug resistance in Africa: strategies for monitoring and deterrence. (Translated from eng) *Curr Top Microbiol Immunol* 295:55-79 (in eng).
23. Bradley D (1996) Malaria. in *Oxford Textbook of Medicine*, ed Weatherall D J (Oxford Medical Publishers), p 835863.
24. Teng R, et al. (2009) Metabolite profiling of the intraerythrocytic malaria parasite *Plasmodium falciparum* by 1H NMR spectroscopy. *NMR in Biomedicine* 22(3):292-302.
25. Wurm M, Schopke B, Lutz D, Mailer J, & Zeng A (Microtechnology meets systems biology: The small molecules of metabolome as next big targets. *Journal of Biotechnology.*
26. Lee H, Sun E, Ham D, & Weissleder R (2008) Chip—NMR biosensor for detection and molecular analysis of cells. *Nature medicine* 14(8):869-874.
27. Lee H, Yoon T, Figueiredo J, Swirski F, & Weissleder R (2009) Rapid detection and profiling of cancer cells in fine-needle aspirates. *Proceedings of the National Academy of Sciences* 106(30):12459.
28. Newman D M, et al. (2008) A magneto-optic route toward the in vivo diagnosis of malaria: preliminary results and preclinical trial data. (Translated from eng) *Biophys J* 95(2):994-1000 (in eng).
29. Metzger W G, Mordmuller B G, & Kremsner P G (1995) Malaria pigment in leucocytes. (Translated from eng) *Trans R Soc Trop Med Hyg* 89(6):637-638 (in eng).
30. Hackett S, Hamzah J, Davis T M, & St Pierre T G (2009) Magnetic susceptibility of iron in malaria-infected red blood cells. (Translated from eng) *Biochim Biophys Acta* 1792(2):93-99 (in eng).
31. Thulborn K R, Waterton J C, Matthews P M, & Radda G K (1982) Oxygenation Dependence of the Transverse Relaxation-Time of Water Protons in Whole-Blood at High-Field. (Translated from English) *Biochimica Et Biophysica Acta* 714(2):265-270 (in English).
32. Lambros C & Vanderberg J P (1979) Synchronization of *Plasmodium falciparum* erythrocytic stages in culture. (Translated from eng) *J Parasitol* 65(3):418-420 (in eng).
33. Ribaut C, et al. (2008) Concentration and purification by magnetic separation of the erythrocytic stages of all human *Plasmodium* species. (Translated from eng) *Malar J* 7:45 (in eng).

34. Crewe W (1993) Basic Malaria Microscopy, Pt 1-2, Learners Guide—World-Hlth-Org. (Translated from English) *Journal of the Royal Society of Health* 113(4):219-219 (in English).
35. Meyer M, Yu O, Eclancher B, Grucker D, & Chambron J (1995) NMR relaxation rates and blood oxygenation level. *Magnetic Resonance in Medicine* 34(2):234-241.
36. Silamut K, et al. (1999) A quantitative analysis of the microvascular sequestration of malaria parasites in the human brain. (Translated from eng) *Am J Pathol* 155(2): 395-410 (in eng).
37. Lwin K M, et al. (2008) Clinically uncomplicated *Plasmodium falciparum* malaria with high schizontaemia: a case report. (Translated from eng) *Malar J* 7:57 (in eng).
38. Phu N H, Day N, Diep P T, Ferguson D J P, & White N J (1995) Intraleukocytic Malaria Pigment and Prognosis in Severe Malaria. (Translated from English) *Transactions of the Royal Society of Tropical Medicine and Hygiene* 89(2):200-204 (in English).
39. Moore L R, et al. (2006) Hemoglobin degradation in malaria-infected erythrocytes determined from live cell magnetophoresis. (Translated from eng) *FASEB J* 20(6): 747-749 (in eng).
40. Hanscheid T (1999) Diagnosis of malaria: a review of alternatives to conventional microscopy. (Translated from eng) *Clin Lab Haematol* 21(4):235-245 (in eng).
41. Eling W (1977) Ficoll fractionation for the separation of parasitized erythrocytes from malaria infected blood. *Bulletin of the World Health Organization* 55(1):105.
42. Hou H W, et al. (2010) Deformability based cell margination—A simple microfluidic design for malaria infected erythrocyte separation. *Lab Chip* 10:2605-2613.
43. Levitt M H (2001) *Spin dynamics: basics of nuclear magnetic resonance* (Wiley).
44. Makler M T, Ries L K, Ries J, Horton R J, & Hinrichs D J (1991) Detection of *Plasmodium falciparum* infection with the fluorescent dye, benzothiocarboxypurine. (Translated from eng) *Am J Trop Med Hyg* 44(1):11-16 (in eng).
45. El-Nageh M M (1996) Coordination for better laboratory services. (Translated from eng) *World Health Forum* 17(2):200-202 (in eng).
46. Quintana M, et al. (1998) Malaria diagnosis by dipstick assay in a Honduran population with coendemic *Plasmodium falciparum* and *Plasmodium vivax*. (Translated from eng) *Am J Trop Med Hyg* 59(6):868-871 (in eng).
47. Sullivan Jr D (Hemozoin: a biocrystal synthesized during the degradation of hemoglobin.
48. G. Webb A (1997) Radiofrequency microcoils in magnetic resonance. *Progress in Nuclear Magnetic Resonance Spectroscopy* 31(1):1-42.
49. Takeda K (2007) A highly integrated FPGA-based nuclear magnetic resonance spectrometer. (Translated from eng) *Rev Sci Instrum* 78(3):033103 (in eng).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

The invention claimed is:

1. A device for performing magnetic resonance relaxometry, the device comprising:

a radio-frequency spectrometer comprising at least one field programmable gate array chip;
a power amplifier electrically connected with the radio-frequency spectrometer and amplifying an electrical output of the radio-frequency spectrometer, thereby producing an amplified electrical signal comprising between about 0.1 Watts and about 10 Watts power;
a duplexer configured to isolate the radio-frequency spectrometer from the amplified electrical signal during a receiving mode of the device wherein the duplexer comprises a passive duplexer without a quarter wavelength transmission cable;
a radio-frequency detection probe configured to transmit radiofrequency electromagnetic radiation to excite nuclei under resonance during a transmission mode of the device, the radio-frequency detection probe comprising a detection microcoil comprising an inner diameter of less than about 1 millimeter; and
at least one magnet supplying an external magnetic field to a detection region of the radio-frequency detection probe, the external magnetic field being less than about 3 Tesla.

2. A device according to claim 1, wherein the at least one magnet comprises at least two permanent magnets separated by a gap of less than about 5 millimeters.

3. A device according to claim 1, wherein the device weighs less than about 0.5 kilograms.

4. A device according to claim 1, wherein the radio-frequency spectrometer, power amplifier and the at least one magnet are mounted on a single circuit board of less than about 500 square centimeters size.

5. A device according to claim 1, wherein the radio-frequency spectrometer comprises a pulse programmer, a direct digital synthesis module, the transmitter and a receiver.

6. A device according to claim 1, wherein the power amplifier comprises at least one surface mount power amplifier module and is mounted on a single circuit board of less than about 20 square centimeter area.

7. A device according to claim 1, wherein the at least one magnet fits within a volume of less than about 30 cubic centimeters.

8. A device according to claim 1, the passive duplexer comprising: a chip inductor in parallel with a fixed capacitor that is in series with a pair of crossed diodes; a trimmer capacitor in series with the parallel combination of the chip inductor, fixed capacitor and pair of crossed diodes; and at least one surface mount radio frequency switch diode.

9. A device according to claim 1, wherein the device is configured to receive a centrifuge tube, which same centrifuge tube is configured to be received in a centrifuge.

10. A device according to claim 1, further comprising a centrifuge tube, at least a portion of the centrifuge tube being inserted into the detection region of the radio-frequency detection probe.

11. A device according to claim 10, wherein the centrifuge tube comprises an outside diameter of less than about 1 millimeter, the centrifuge tube comprising a blood sample including blood from an animal body.

12. A device according to claim 1, wherein the device is configured to perform at least one of Nuclear Magnetic Resonance (NMR) and Magnetic Resonance Imaging (MRI).

13. A device according to claim 1, further comprising a sample comprising a micro-organism, at least a portion of the sample being inserted into the detection region of the radio-frequency detection probe.

14. A device according to claim 1, further comprising an item to be imaged, at least a portion of the item to be imaged being inserted into the detection region of the radio-frequency detection probe.

15. A device according to claim 1, further comprising a biological sample, at least a portion of the biological sample being inserted into the detection region of the radio-frequency detection probe.

16. A device according to claim 15, wherein the biological sample is capable of producing an indication of a stress level on a biological organism through magnetic resonance.

17. A device according to claim 15, wherein the biological sample comprises a biomarker of a disease, the biomarker being detectable by magnetic resonance.

* * * * *